(12) United States Patent
Johansson

(10) Patent No.: US 8,685,958 B2
(45) Date of Patent: *Apr. 1, 2014

(54) THERAPEUTIC AGENTS

(75) Inventor: Lars Anders Mikael Johansson, Mölndal (SE)

(73) Assignee: AstraZeneca AB, Södertälje (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/548,396

(22) Filed: Jul. 13, 2012

(65) Prior Publication Data

US 2013/0184250 A1  Jul. 18, 2013

Related U.S. Application Data

(60) Provisional application No. 61/508,133, filed on Jul. 15, 2011.

(51) Int. Cl.
*C07D 491/107* (2006.01)

(52) U.S. Cl.
USPC ....... 514/210.18; 548/143; 548/409; 548/953

(58) Field of Classification Search
USPC .............. 514/210.81; 548/143, 409, 953
See application file for complete search history.

(56) References Cited

U.S. PATENT DOCUMENTS

| | | | |
|---|---|---|---|
| 4,212,867 | A | 7/1980 | Boesch |
| 7,723,331 | B2 | 5/2010 | Giordanetto et al. |
| 8,110,566 | B2 | 2/2012 | Johansson et al. |
| 2005/0176795 | A1 | 8/2005 | Schwink et al. |
| 2005/0222161 | A1 | 10/2005 | Moriya et al. |
| 2008/0269275 | A1 | 10/2008 | Brown et al. |
| 2008/0300232 | A1 | 12/2008 | Brickmann et al. |
| 2008/0306055 | A1 | 12/2008 | Egner et al. |
| 2009/0076064 | A1 | 3/2009 | Urbanek et al. |

FOREIGN PATENT DOCUMENTS

| | | |
|---|---|---|
| EP | 1593667 | 11/2005 |
| JP | 2006176443 | 7/2006 |
| WO | WO 2004/004726 | 1/2004 |
| WO | WO 2005/066132 | 7/2005 |
| WO | WO 2005/070902 | 8/2005 |
| WO | WO 2005/090330 | 9/2005 |
| WO | WO 2006/019833 | 2/2006 |
| WO | WO 2006/044228 | 4/2006 |
| WO | WO 2006/066173 | 6/2006 |
| WO | WO 2006/068594 | 6/2006 |
| WO | WO 2006/125665 | 11/2006 |
| WO | WO 2006/130075 | 12/2006 |
| WO | WO 2006/136924 | 12/2006 |
| WO | WO 2007/011284 | 1/2007 |
| WO | WO 2007/078251 | 7/2007 |
| WO | WO 2008/011453 | 1/2008 |
| WO | WO 2008/020799 | 2/2008 |
| WO | WO 2008/068265 | 6/2008 |
| WO | WO 2008/076562 | 6/2008 |
| WO | WO 2008/131103 | 10/2008 |
| WO | WO 2009/024502 | 2/2009 |
| WO | WO 2009/052062 | 4/2009 |
| WO | WO 2009/135842 | 11/2009 |
| WO | WO 2010/125390 | 11/2010 |

OTHER PUBLICATIONS

International Search Report and Written Opinion for PCT/GB2010/050698, dated Jul. 30, 2010.
International Search Report and Written Opinion for PCT/GB2011/051256, dated Jan. 23, 2012.
Johansson, "Recent progress in the discovery of melanin-concentrating hormone 1-receptor anatagonists," Expert Opinion in Therapeutic Patents, 21(6):905-925 (2011).
Mendez-Andino et al., "MCH-R1 antagonists: what is keeping most research programs away from the clinic?," Drug Discovery Today, 12(21/22):972-979 (2007).
Sheng et al., "Design, synthesis and evaluation of 2-phenoxy-indan-1-one derivatives as acetylcholinesterase inhibitors," Bioorganic & Medicinal Chemistry Letters, 15(17):3834-3837 (2005).
Wuitschik et al., "Spirocyclic Oxetanes: synthesis and properties", Angew. Chem. Int. Ed. 47: 4512-4515 (2008).

*Primary Examiner* — San-Ming Hui
*Assistant Examiner* — Kathrien Cruz
(74) *Attorney, Agent, or Firm* — Morgan, Lewis & Bockius LLP

(57) ABSTRACT

Disclosed herein are azetidinyl compounds of formula I,

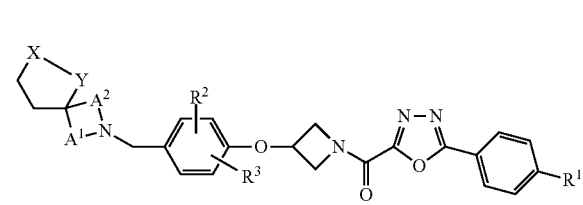

I as described herein, pharmaceutical compositions comprising an azetidinyl compound, and a method of using an azetidinyl compound in the treatment or prophylaxis of a melanin-concentrating hormone related disease or condition.

13 Claims, No Drawings

THERAPEUTIC AGENTS

This application claims the benefit under 35 U.S.C. §119 (e) of U.S. Provisional Application No. 61/508133, filed on Jul. 15, 2011 and which is incorporated by reference herein in its entirety.

FIELD OF INVENTION

The present invention relates to certain (3-(4-(spiroheterocyic)methyl)phenoxy)-azetidin-1-yl)(5-(phenyl)-1,3,4-oxadiazol-2-yl)methanone compounds of formula I, to processes for preparing such compounds, to their use in the treatment of a melanin-concentrating hormone related disease or condition for example obesity, obesity-related conditions, anxiety and depression, and to pharmaceutical compositions containing them.

BACKGROUND OF THE INVENTION

The actions of melanin-concentrating hormone (MCH) are thought to be involved in anxiety, depression, obesity, and obesity-related disorders. MCH has been found to be a major regulator of eating behaviour and energy homeostasis and is the natural ligand for the 353-amino acid orphan G-protein-coupled-receptor (GPCR) termed SLC-1 (also known as GPR24). SLC-1 is sequentially homologous to the somatostatin receptors, and is frequently referred to as the "melanin-concentrating hormone receptor" (MCH receptor type 1, MCH1 receptor, or MCHR1).

In mice lacking the MCH1 receptor, there is no increased feeding response to MCH, and a lean phenotype is seen, suggesting that this receptor is responsible for mediating the feeding effect of MCH. MCH receptor antagonists have also been shown to block the feeding effects of MCH, and to reduce body weight & adiposity in diet-induced obese mice. The conservation of distribution and sequence of MCH1 receptors suggest a similar role for this receptor in man and rodent species. Hence, MCH receptor antagonists have been proposed as a treatment for obesity and other disorders characterised by excessive eating and body weight.

Emerging evidence also suggests that MCHR1 plays a role in the regulation of mood and stress. Within the central nervous system, MCHR1 mRNA and protein are distributed in various hypothalamic nuclei including, for example, the paraventricular nucleus (PVN) and the nucleus accumbens shell; and limbic structures including, for example, the hippocampus, septum, amygdala, locus coeruleus and dorsal raphe nucleus, all of which are thought to be involved in the regulation of emotion and stress.

Introduction of MCH into the medial preoptic area has been reported to induce anxiety, although contrary anxiolytic-like effects of MCH injection have also been reported. Injection of MCH into the nucleus accumbens shell, in which MCHR1 is abundant, decreased mobility in a forced swim test in rats, suggesting a depressive effect. Also, it has been reported that MCHR1 antagonists exhibited antidepressant and anxiolytic-like effects in rodent tests, suggesting a role for MCHR1 in depression and anxiety.

MCH antagonists are thus thought likely to provide benefit to numerous people and to have a potential to alleviate anxiety and depression and be useful for treating obesity and obesity-related conditions.

MCH receptor antagonists having a bicyclic central core are disclosed in WO2006/066173 (benzothiazole or benzoxazole central core) and US2005/0222161 (benzimuidazole core).

Our co-pending application WO 2010/125390 discloses a compound of formula A

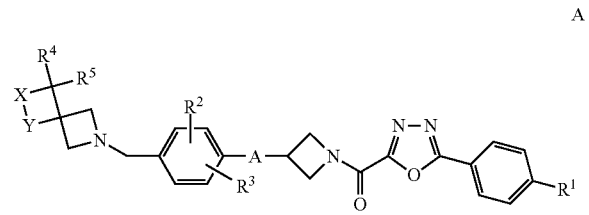

or a pharmaceutically acceptable salt thereof in which
$R^1$ represents H, fluoro, chloro, bromo, cyano, a $C_{1-3}$alkyl group optionally substituted by one or more fluoro, or a $C_{1-2}$alkoxy group optionally substituted by one or more fluoro; A represents O or S;
$R^2$ and $R^3$ independently represent H, fluoro, chloro, bromo, a $C_{1-4}$alkyl group optionally substituted by one or more fluoro, or a $C_{1-4}$alkoxy group optionally substituted by one or more fluoro; provided that $R^2$ and $R^3$ are not located meta to each other;
$R^4$ and $R^5$ independently represent H or a $C_{1-4}$alkyl group; and
X and Y independently represent O or $CH_2$ with the proviso that X and Y are different; and the use of such compounds in the treatment of a melanin-concentrating hormone related disease or condition for example obesity, obesity-related conditions, anxiety and depression. The compounds disclosed in WO 2010/125390 are spiro compounds having two four-membered rings fused to each other. The present application does not cover such compounds as the present application is directed to spiro compounds having at least one five-membered ring.

Our co-pending application WO 2012/004588 discloses a compound of formula B

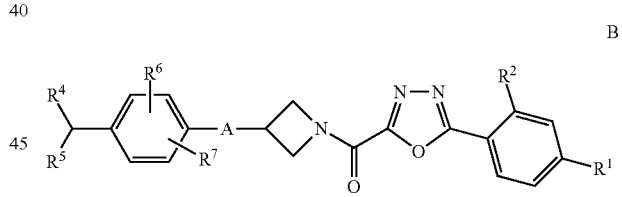

or a pharmaceutically acceptable salt thereof in which
$R^1$ represents H, fluoro, chloro, bromo, cyano, a $C_{1-4}$alkyl group optionally substituted by one or more fluoro, a $C_{1-2}$alkoxy group optionally substituted by one or more fluoro, or a $C_{1-3}$alkylthio group optionally substituted by one or more fluoro;
$R^2$ represents H or fluoro;
$R^4$ represents a group of formula $—NR^aR^b$ in which
a) $R^a$ and $R^b$ independently represent: 1) H 2) a $C_{1-4}$alkyl group optionally substituted by one or more of the following: fluoro, hydroxy, a $C_{1-4}$alkoxy group, or a $C_{3-6}$cycloalkyl group, wherein the $C_{3-6}$cycloalkyl group is optionally substituted by one or more of the following: hydroxy, a $C_{1-4}$alkoxy group or fluoro 3) a $C_{3-6}$cycloalkyl group optionally substituted by one or more of the following: hydroxy, a $C_{1-4}$alkoxy group or fluoro 4) a $C_{1-4}$alkoxy $C_{2-4}$alkylene group in which the alkylene chain is optionally substituted by one or more $C_{1-4}$alkyl groups or 5) $R^a$ represents H, a $C_{1-4}$alkyl group or a $C_{3-6}$cycloalkyl group and $R^b$ represents a group -L-$R^8$ in which L represents a bond or a $C_{1-4}$alkylene chain optionally substituted by one or more $C_4$alkyl groups and $R^8$ represents a carbon linked 4-7 membered saturated monocyclic heterocyclic ring containing 1 or 2 hetero atoms selected from oxygen and nitrogen optionally substituted by one or more of the following: hydroxy, a $C_{1-4}$alkyl group, a $C_{1-4}$alkoxy group or a $C_{1-4}$alkanoyl group; or b) $R^a$ and $R^b$ together with the nitrogen atom to which they are attached represent a saturated 4 to 7 membered monocyclic heterocyclic ring optionally containing an additional oxygen, sulphur, SO or $SO_2$ provided that this additional atom or group is always separated from the nitrogen atom by at least two carbon atoms and wherein the ring is optionally substituted by one or more of the following: fluoro, hydroxy, a $C_{1-4}$alkoxy group, a $C_{1-4}$alkoxycarbonyl group, a $C_{3-6}$cycloalkyl group, or a $C_{1-4}$alkyl group optionally substituted by hydroxy or by a $C_{1-4}$alkoxy group or by one or more fluoro, provided that the substituents linked to the ring by a hetero atom are not located at a carbon atom adjacent to any ring hetero atom; or c) $R^a$ and $R^b$ together with the nitrogen atom to which they are attached represent a saturated 4 to 7 membered monocyclic heterocyclic ring containing an additional nitrogen optionally substituted at the additional nitrogen atom by a $C_{1-4}$alkanoyl group, benzoyl, a $C_{1-4}$alkoxycarbonyl group, a $C_{1-4}$alkylsulfonyl group; carbamoyl, N—$C_{1-4}$alkylcarbamoyl, N, N-di$C_{1-4}$alkylcarbamoyl or $C_{1-4}$alkyl group;

$R^5$ represents H or a $C_{1-3}$alkyl group optionally substituted by one or more fluoro or one of the following: hydroxy or a $C_{1-4}$alkoxy group;

$R^6$ and $R^7$ independently represent H, fluoro, chloro, bromo, a $C_{1-4}$alkyl group optionally substituted by one or more fluoro, a $C_{1-4}$alkoxy group optionally substituted by one or more fluoro; provided that $R^6$ and $R^7$ are not located meta to each other; and A represents O or S; and the use of such compounds in the treatment of a melanin-concentrating hormone related disease or condition for example obesity, obesity-related conditions, anxiety and depression.

SUMMARY OF THE INVENTION

The present invention provides compounds that are MCH receptor antagonists and therefore are likely to be useful in the treatment of anxiety, depression, obesity and obesity-related conditions.

DESCRIPTION OF THE INVENTION

The present invention provides a compound of formula I

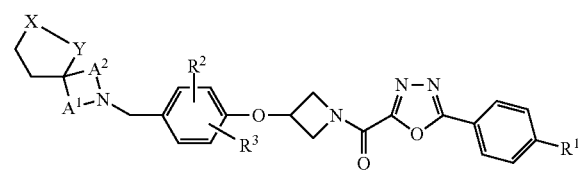

I or a pharmaceutically acceptable salt thereof in which
$R^1$ represents H, $C_{1-3}$alkoxy optionally substituted by one or more fluoro or a $C_{1-3}$alkyl group optionally substituted by one or more fluoro;

$R^2$ and $R^3$ independently represent H, fluoro, chloro, bromo, a $C_{1-3}$alkyl group optionally substituted by one or more fluoro, or a $C_{1-3}$alkoxy group optionally substituted by one or more fluoro provided that $R^2$ and $R^3$ are not located meta to each other;

$A^1$ represents a bond, $CH_2$ or $CH_2$—$CH_2$;

$A^2$ represents a bond, $CH_2$, $CH_2$—$CH_2$ or $CH_2$—$CH_2$—$CH_2$; provided that the total number of carbons in $A^1$ and $A^2$ together is 2 or 3;

X represents a bond, $CH_2$ or O; and

Y represents a bond, $CH_2$ or O;

with the provisos that 1) one and only one of X and Y is always O and 2) when $A^1$ and $A^2$ each represent $CH_2$ then one of X and Y is $CH_2$.

The present invention provides a compound of formula IA

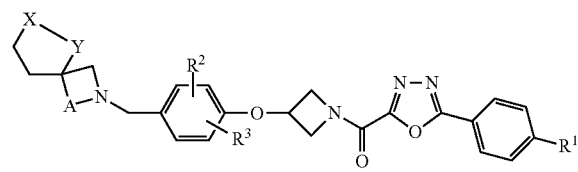

IA or a pharmaceutically acceptable salt thereof in which $R^1$ represents H, $C_{1-3}$alkoxy optionally substituted by one or more fluoro or a $C_{1-3}$alkyl group optionally substituted by one or more fluoro;

$R^2$ and $R^3$ independently represent H, fluoro, chloro, bromo, a $C_{1-3}$alkyl group optionally substituted by one or more fluoro, or a $C_{1-3}$alkoxy group optionally substituted by one or more fluoro;

A represents $CH_2$ or $CH_2$—$CH_2$;

X represents a bond, $CH_2$ or O; and

Y represents a bond, $CH_2$ or O;

with the provisos that 1) one and only one of X and Y is always O and 2) when A is $CH_2$ and one of X and Y is O then the other one of X and Y is $CH_2$.

In another aspect the present invention provides a compound of formula I represented by formula II

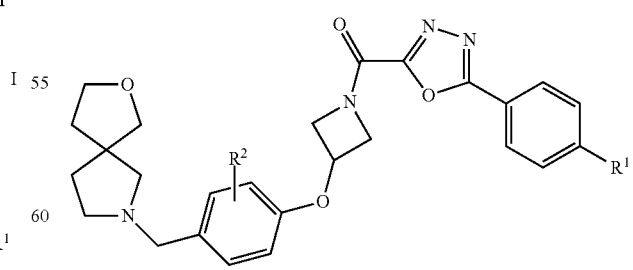

II or a pharmaceutically acceptable salt thereof in which
$R^1$ represents H, methoxy or difluoromethyl; and
$R^2$ represents H, methyl or methoxy.

In another aspect the present invention provides a compound of formula I represented by formula IIA

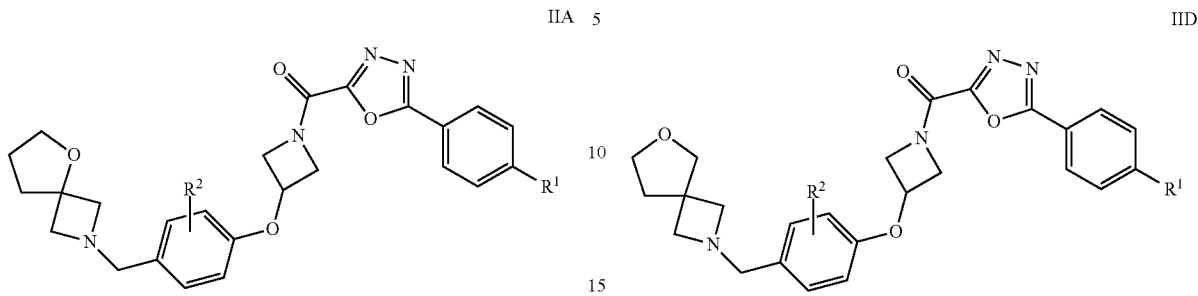

IIA to or a pharmaceutically acceptable salt thereof in which
R¹ represents H, methoxy or difluoromethyl; and
R² represents H, methyl or methoxy.

In a further embodiment the present invention provides a compound of formula IIB

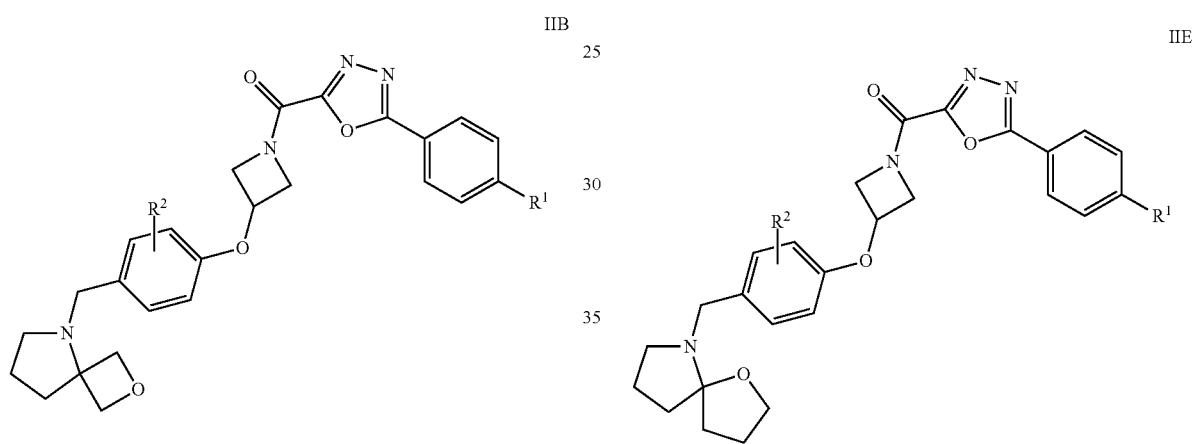

IIB or a pharmaceutically acceptable salt thereof in which
R¹ represents H, methoxy or difluoromethyl; and
R² represents H, methyl or methoxy.

In a further embodiment the present invention provides a compound of formula IIC

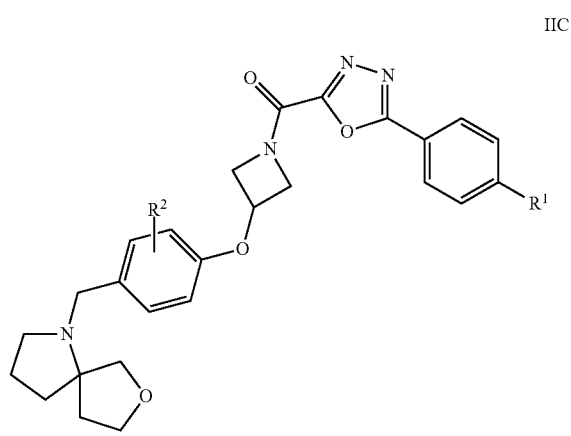

IIC or a pharmaceutically acceptable salt thereof in which
R¹ represents H, methoxy or difluoromethyl; and
R² represents H, methyl or methoxy.

In a further embodiment the present invention provides a compound of formula IID

IID or a pharmaceutically acceptable salt thereof in which
R¹ represents H, methoxy or difluoromethyl; and
R² represents H, methyl or methoxy.

In a further embodiment the present invention provides a compound of formula IIE

IIE or a pharmaceutically acceptable salt thereof in which
R¹ represents H, methoxy or difluoromethyl; and
R² represents H, methyl or methoxy.

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I) (including formulae II, IIA, IIB, IIC, IID and IIE). Further, each of the following values may be used in combination with one or more of the other following values to limit the broadest definition, or any sub-definition, of formula (I) (including formulae II, IIA, IIB, IIC, IID and IIE). It should be understood however that the limitations of the provisos will be observed in applying these combinations.

1) $R^1$ represents $C_{1-2}$ alkoxy optionally substituted by one or more fluoro.
2) $R^1$ represents $C_{1-2}$ alkyl optionally substituted by one or more fluoro.
3) $R^1$ represents H, methoxy or difluoromethyl.
4) $R^1$ represents H or methoxy.
5) $R^1$ represents H.
6) $R^1$ represents methoxy.
7) $R^2$ represents H.
8) $R^2$ represents methyl.
9) $R^2$ represents methoxy.

10) R² and R³ independently represent H, fluoro, a C$_{1-2}$alkyl group optionally substituted by one or more fluoro, or a C$_{1-2}$alkoxy group optionally substituted by one or more fluoro;
11) a) R² and R³ independently represent fluoro, chloro, bromo, a C$_{1-3}$alkyl group optionally substituted by one or more fluoro, or a C$_{1-3}$alkoxy group optionally substituted by one or more fluoro or particularly b) R² and R³ independently represent fluoro, a C$_{1-2}$alkyl group optionally substituted by one or more fluoro, or a C$_{1-2}$alkoxy group optionally substituted by one or more fluoro and in either case a) or b) R² and R³ are not located meta to each other;
12) a) R² and R³ independently represent fluoro, chloro, bromo, a C$_{1-3}$alkyl group optionally substituted by one or more fluoro, or a C$_{1-3}$alkoxy group optionally substituted by one or more fluoro or more fluoro or particularly b) R² and R³ independently represent fluoro, a C$_{1-2}$alkyl group optionally substituted by one or more fluoro, or a C$_{1-2}$alkoxy group optionally substituted by one or more fluoro and in either case a) or b) R² and R³ are located ortho to each other:
13) R² and R³ are identical.
14) A¹ represents CH$_2$.
15) A¹ represents CH$_2$—CH$_2$.
16) A² represents CH$_2$.
17) A² represents CH$_2$—CH$_2$.
18) A² represents CH$_2$—CH$_2$—CH$_2$.
19) A represents CH$_2$.
20) A represents CH$_2$—CH$_2$.
21) X represents a bond.
22) X represents CH$_2$.
23) X represents O.
24) Y represents a bond.
25) Y represents CH$_2$.
26) Y represents O.

The terms "C$_{1-3}$alkyl" refers to a straight or branched chain alkane radical containing from 1 to 3 carbon atoms. Exemplary groups include methyl; ethyl; and propyl; isopropyl.

The term "C$_{1-3}$alkoxy" refers to groups of the general formula —OR$^a$, wherein R$^a$ is selected from a C$_{1-3}$alkyl. Exemplary groups include methoxy, ethoxy, propoxy and isopropoxy.

In a further aspect the present invention provides one or more of the following compounds:
(3-(4-(2-oxa-7-azaspiro[4.4]nonan-7-ylmhethyl)phenoxy)azetidin-1-yl)(5-(4-methoxyphenyl)-1,3,4-oxadiazol-2-yl)methanone;
(+)-(3-(4-(2-oxa-7-azaspiro[4.4]nonan-7-ylmhethyl)phenoxy)azetidin-1-yl)(5-(4-methoxyphenyl)-1,3,4-oxadiazol-2-yl)methanone;
(−)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone;
(3-(4-(5-oxa-2-azaspiro[3.4]octan-2-ylmethyl)phenoxy)azetidin-1-yl)(5-(4-methoxyphenyl)-1,3,4-oxadiazol-2-yl)methanone;
(3-(4-(6-oxa-2-azaspiro[3.4]octan-2-ylmethyl)phenoxy)azetidin-1-yl)(5-(4-methoxyphenyl)-1,3,4-oxadiazol-2-yl)methanone;
(3-(4-(2-oxa-7-azaspiro[4.4]nonan-7-ylmethyl)phenoxy)azetidin-1-yl)(5-phenyl-1,3,4-oxadiazol-2-yl)methanone;
(+)-(3-(4-(2-oxa-7-azaspiro[4.4]nonan-7-ylmethyl)phenoxy)azetidin-1-yl)(5-phenyl-1,3,4-oxadiazol-2-yl)methanone;
(−)-(3-(4-(2-oxa-7-azaspiro[4.4]nonan-7-ylmethyl)phenoxy)azetidin-1-yl)(5-phenyl-1,3,4-oxadiazol-2-yl)methanone;
(3-(4-(6-oxa-2-azaspiro[3.4]octan-2-ylmethyl)phenoxy)azetidin-1-yl)(5-phenyl-1,3,4-oxadiazol-2-yl)methanone;
(3-(4-(5-oxa-2-azaspiro[3.4]octan-2-yl-methyl)phenoxy)azetidin-1-yl)(5-phenyl-1,3,4-oxadiazol-2-yl)methanone;
(3-(4-(6-oxa-2-azaspiro[3.4]octan-2-ylmethyl)-3-methylphenoxy)azetidin-1-yl)(5-phenyl-1,3,4-oxadiazol-2-yl)methanone;
(3-(4-(2-oxa-7-azaspiro[4.4]nonan-7-ylmethyl)-3-methylphenoxy)azetidin-1-yl)(5-phenyl-1,3,4-oxadiazol-2-yl)methanone;
(+)-(3-(4-(2-oxa-7-azaspiro[4.4]nonan-7-ylmethyl)-3-methylphenoxy)azetidin-1-yl)(5-phenyl-1,3,4-oxadiazol-2-yl)methanone;
(−)-(3-(4-(2-oxa-7-azaspiro[4.4]nonan-7-ylmethyl)-3-methylphenoxy)azetidin-1-yl) (5-phenyl-1,3,4-oxadiazol-2-yl)methanone;
(3-(4-(5-oxa-2-azaspiro[3.4]octan-2-ylmethyl)-3-methylphenoxy)azetidin-1-yl)(5-phenyl-1,3,4-oxadiazol-2-yl)methanone;
(3-(4-(2-oxa-5-azaspiro[3.4]octan-5-ylmethyl)phenoxy)azetidin-1-yl)(5-(4-methoxyphenyl)-1,3,4-oxadiazol-2-yl)methanone;
(3-(4-(2-oxa-5-azaspiro[3.4]octan-5-ylmethyl)phenoxy)azetidin-1-yl)(5-phenyl-1,3,4-oxadiazol-2-yl)methanone;
(3-(4-(7-oxa-1-azaspiro[4.4]nonan-1-ylmethyl)phenoxy)azetidin-1-yl)(5-(4-methoxyphenyl)-1,3,4-oxadiazol-2-yl)methanone;
(+)-(3-(4-(7-oxa-1-azaspiro[4.4]nonan-1-ylmethyl)phenoxy)azetidin-1-yl)(5-(4-methoxyphenyl)-1,3,4-oxadiazol-2-yl)methanone;
(−)-(3-(4-(7-oxa-1-azaspiro[4.4]nonan-1-ylmethyl)phenoxy)azetidin-1-yl)(5-(4-methoxyphenyl)-1,3,4-oxadiazol-2-yl)methanone;
(3-(4-(7-oxa-1-azaspiro[4.4]nonan-1-ylmethyl)phenoxy)azetidin-1-yl)(5-phenyl-1,3,4-oxadiazol-2-yl)methanone;
(+)-(3-(4-(7-oxa-1-azaspiro[4.4]nonan-1-ylmethyl)phenoxy)azetidin-1-yl)(5-phenyl-1,3,4-oxadiazol-2-yl)methanone;
(−)-(3-(4-(7-oxa-1-azaspiro[4.4]nonan-1-ylmethyl)phenoxy)azetidin-1-yl)(5-phenyl-1,3,4-oxadiazol-2-yl)methanone;
(3-(4-(2-oxa-5-azaspiro[3.4]octan-5-ylmethyl)-3-methoxyphenoxy)azetidin-1-yl)(5-phenyl-1,3,4-oxadiazol-2-yl)methanone;
(3-(4-(2-oxa-5-azaspiro[3.4]octan-5-ylmethyl)-2-methoxyphenoxy)azetidin-1-yl)(5-phenyl-1,3,4-oxadiazol-2-yl)methanone;
(3-(4-(2-oxa-5-azaspiro[3.4]octan-5-ylmethyl)-2-methoxyphenoxy)azetidin-1-yl)(5-(4-(difluoromethyl)phenyl)-1,3,4-oxadiazol-2-yl)methanone;
(3-(4-(2-oxa-5-azaspiro[3.4]octan-5-ylmethyl)-3-methoxyphenoxy)azetidin-1-yl)(5-(4-(difluoromethyl)phenyl)-1,3,4-oxadiazol-2-yl)methanone;
(3-(4-(1-oxa-7-azaspiro[4.4]nonan-7-ylmethyl)phenoxy)azetidin-1-yl)(5-(4-methoxyphenyl)-1,3,4-oxadiazol-2-yl)methanone; and
(3-(4-(1-oxa-7-azaspiro[4.4]nonan-7-ylmethyl)phenoxy)azetidin-1-yl)(5-phenyl-1,3,4-oxadiazol-2-yl)methanone;
or a pharmaceutically acceptable salt thereof.

The present invention also provides one of the compounds from the above list or any number of the above compounds between 1 and 29. In another aspect the present invention provides a compound of formula I (including formulae II, IIA, IIB, IIC, IID and IIE) as defined in any of the definitions above but excluding any one or more of the compounds in the list of compounds immediately above.

From this point onward in the description a compound of formula I includes in the alternative a compound of each of the following formulae: II, IIA, IIB, IIC, IID and IIE.

Further described herein is a pharmaceutical composition comprising a compound of formula I, or a pharmaceutically acceptable salt thereof, and a pharmaceutically acceptable carrier and/or diluent.

Yet further described herein is a method for treatment or prophylaxis of a disease or condition in which modulation of the MCH1 receptor is beneficial comprising administering to a wan-blooded animal in need of such treatment or prophylaxis a therapeutically-effective amount of a compound of formula I, or a pharmaceutically acceptable salt thereof.

Yet still further described herein is the use of a compound according to formula I, or a pharmaceutically acceptable salt thereof, or mixtures thereof for the treatment or prophylaxis of a disease or condition in which modulation of the MCH1 receptor is beneficial.

Even further described herein is use of a compound according to formula I, or pharmaceutically acceptable salts thereof, or mixtures thereof in the manufacture of a medicament for the treatment or prophylaxis of a disease or condition in which modulation of the MCH1 receptor is beneficial.

Still further described herein is the use a compound of formula I, or a pharmaceutically acceptable salt thereof, as a medicament.

The term "MCHR" refers to the melanin-concentrating hormone receptor protein 1 (MCHR1), unless otherwise stated.

The terms "treat", "treating", and "treatment" refer to modulation of a disease and/or its attendant symptoms.

The terms "prevent", "preventing", and "prevention" refer to decreasing or eliminating a disease and/or its attendant symptoms.

The terms "modulate", "modulates", "modulating", or "modulation", as used herein, refer to, for example, the activation (e.g., agonist activity) or inhibition (e.g., antagonist activity) of at least one MCHR.

The term "pharmaceutically-acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The terms "prophylaxis", as used herein, refer to (i) preventing the development of a disease and/or condition; and/or (ii) protecting against worsening of a disease and/or condition in a situation where the disease and/or condition has developed.

As used herein, the term "MCHR-mediated condition or disease" refers to a condition or disease amenable to modulation by an MCHR active agent.

The term "therapeutically-effective amount" refers to that amount of a compound sufficient to modulate one or more of the symptoms of the condition or disease being treated.

A further embodiment relates to compounds as described herein wherein one or more of the atoms is an isotope of the same element for example $^{11}C$, $^{13}C$, $^{14}C$ or deuterium. In a particular embodiment, the compound is labelled with tritium. Such isotopically labelled compounds are synthesized either by incorporating labelled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

A compound labelled with tritium may be useful in identifying novel medicinal compounds capable of binding to and modulating the activity, by agonism, partial agonism, or antagonism, of an MCH1 receptor. Such tritium-labelled compounds may be used in assays that measure the displacement of such compounds to assess the binding of ligands that bind to MCH1 receptors.

In an even further embodiment, compounds disclosed herein may additionally comprise one or more atoms of an isotope. In a particular form of this embodiment, a compound comprises an isotopic halogen. Such labelled compounds are synthesized by incorporating labelled starting materials by known methods. In a particular embodiment, the isotope is selected from $^{18}F$, $^{123}I$, $^{125}I$, $^{131}I$, $^{75}Br$, $^{76}Br$, $^{77}Br$ or $^{82}Br$. In a more particular embodiment, the isotope is $^{18}F$.

It will be understood that when compounds of the present invention contain one or more chiral centers for example compounds of formula I, II or IIC, the compounds of the invention may exist in, and be isolated as, enantiomeric or diastereomeric forms, or as a racemic mixture. The present invention includes any possible enantiomers, diastereomers, racemates, or mixtures thereof, of the compounds of formula I. The optically active forms of the compound of the invention may be prepared, for example, by chiral chromatographic separation of a racemate for example using a Chiralpak® IA column (supplied by Chiral Technologies Europe) or a Chiralcel® OJ column (supplied by Chiral Technologies Europe), by synthesis from optically active starting materials or by asymmetric synthesis based on the procedures described hereafter.

It will further be understood that the present invention encompasses tautomers of the compounds of formula I.

It will be understood that certain compounds of the invention may exist in solvated, for example hydrated, as well as unsolvated forms. It will further be understood that the present invention encompasses all such solvated forms of the compounds of formula I. It will further be understood that the present invention encompasses all crystalline forms of such solvates.

The compounds of formula I can also form salts. As a result, when a compound of formula I is referred to herein, such reference includes, unless otherwise indicated, salts thereof. In one embodiment, the compounds of formula I form pharmaceutically acceptable salts. In another embodiment, the compounds of formula I form salts that can, for example, be used to isolate and/or purify the compounds of formula I. It will be understood that the present invention encompasses any and all crystalline forms of such salts and any solvates of such salts and any crystalline forms of any solvates of these salts.

Generally, pharmaceutically acceptable salts of a compound in accordance with formula I can be obtained by using standard procedures well known in the art. These standard procedures include, but are not limited to, for example, the reacting of a sufficiently basic compound, such as, for example, an alkyl amine with a suitable acid, such as, for example, hydrochloric acid or acetic acid, to afford a physiologically acceptable anion.

In one embodiment, a compound in accordance with formula I may be converted to a pharmaceutically acceptable salt or solvate thereof, particularly, an acid addition salt, such as, for example, hydrochloride, hydrobromide, phosphate, acetate, fumarate, maleate, tartrate, citrate, methanesulphonate (mesylate), and p-toluenesulphonate. Particularly preferred salts are the hydrochloride salt and the mesylate salt.

In general, the compounds of formula I can be prepared in accordance with the following processes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art. Combinatorial techniques can be employed in the preparation of compounds, for example, where the intermediates possess groups suitable for these techniques.

Compounds of formula I may be prepared by
a) reacting a compound of formula III

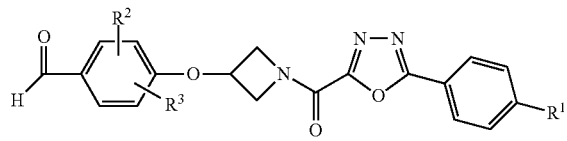

III in which $R^1$, $R^2$ and $R^3$ are as previously defined with a compound of formula IV

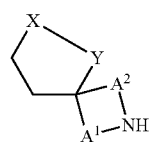

IV or a salt thereof in which $A^1$, $A^2$, X and Y are as previously defined in the presence of a reducing agent, such as sodium triacetoxyborohydride in an appropriate solvent, such as dichloromethane, and optionally in the presence of a base, for example triethylamine or N,N-diisopropylethylamine, if a salt of IV is used at a temperature in the range of 0 to 150° C., particularly in the range of 5 to 30° C.; or
b) reacting a compound of formula V

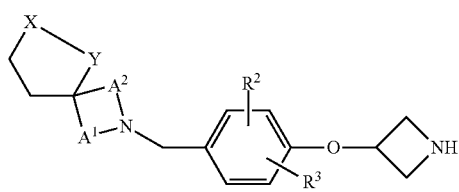

V in which $R^2$, $R^3$, $A^1$, $A^2$, X and Y are as previously defined with a compound of formula VI

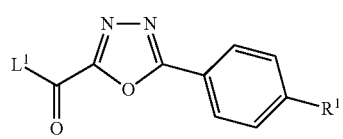

VI in which $R^1$ is as previously defined and $L^1$ represents a leaving group for example a $C_{1-4}$alkoxy group in an appropriate solvent, such as an alcohol for example methanol, at a temperature in the range of 0 to 150° C., particularly in the range of 5 to 30° C. and optionally in the presence of a catalyst for example sodium cyanide.

Compounds of formula III may be prepared by reacting a compound of formula VII

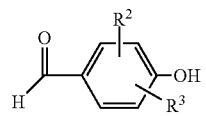

VII in which $R^2$ and $R^3$ are as previously defined with a compound of formula VIII

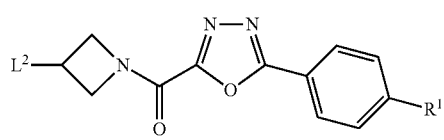

VIII in which $R^1$ is as previously defined and $L^2$ represents a leaving group, for example mesyloxy or tosyloxy, in the presence of a base, for example $Cs_2CO_3$, optionally in the presence of a solvent, for example DMF or preferably DMA, and at a temperature in the range of 0 to 150° C. particularly in the range of 50 to 120° C.

Compounds of formula V may be prepared by reacting a compound of formula IX

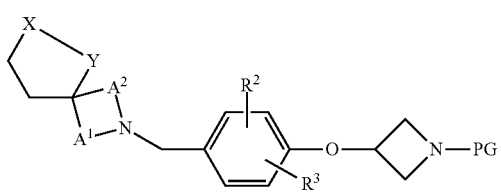

IX in which $R^2$, $R^3$, $A^1$, $A^2$, X and Y are as previously defined and PG represents an amine protecting group, such as an alkoxycarbonyl group, for example tert-butoxycarbonyl, with a deprotecting agent such as an acid, for example trifluoroacetic acid, at a temperature in the range of 0 to 150° C. particularly in the range of 5 to 30° C.

Compounds of formula IX may be prepared by reacting a compound of formula X

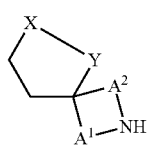

X in which A¹, A², X and Y are as previously defined with a compound of formula XI

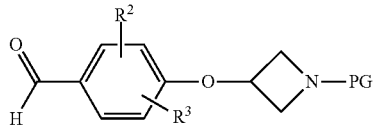

in which R², R³, A¹ and A² are as previously defined and PG represents an amine protecting group, for example an alkoxycarbonyl group, for example tert-butoxycarbonyl.

Certain compounds or formulae I, IV, V and IX are believed to be novel and are herein claimed as a further aspect of the present invention. In a preferred aspect of the invention these compounds are in substantially pure form e.g. greater than 50% pure, particularly greater than 95% pure and more particularly more than 99% pure.

A further embodiment is directed to a method for treatment or prophylaxis of a disease or condition in which modulation of the MCH1 receptor is beneficial comprising administering to a warm-blooded animal in need of such treatment or prophylaxis a therapeutically effective amount of a compound of formula I or a pharmaceutically-acceptable salt thereof.

A more particular embodiment relates to a method for treatment or prophylaxis of a disease or condition in which modulation of the MCH1 receptor is beneficial comprising administering to a warm-blooded animal in need of such treatment or prophylaxis a therapeutically effective amount of an antagonistic compound of formula I.

A further embodiment is directed to the use of a compound in accordance with formula I, or pharmaceutically acceptable salts thereof, or mixtures thereof for the treatment or prophylaxis of a disease or condition in which modulation of the MCH1 receptor is beneficial.

A more particular embodiment relates to the use of antagonistic-compounds of formula I, or a pharmaceutically acceptable salt thereof, for the treatment or prophylaxis of a disease or condition in which modulation of the MCH1 receptor is beneficial.

Yet a further embodiment is directed to the use of a compound in accordance with formula I, or a pharmaceutically acceptable salts thereof, in the manufacture of a medicament for the treatment or prophylaxis of a disease or condition in which modulation of the MCH1 receptor is beneficial.

Still yet a further embodiment is directed to a compound in accordance with formula I, or a pharmaceutically acceptable salt thereof, for use as a medicament.

Another embodiment is directed to a pharmaceutical composition comprising a compound in accordance with formula I, or a pharmaceutically acceptable salt thereof and a pharmaceutically acceptable carrier and/or diluent.

A further embodiment relates to a pharmaceutical composition useful for treatment or prophylaxis of a disease or condition mentioned herein arising from dysfunction of MCH1 receptors in a warm blooded animal comprising a therapeutically-effective amount of a compound of formula I, or pharmaceutically-acceptable salt thereof, for the treatment or prophylaxis of such disease or condition, and at least one pharmaceutically-acceptable carrier and/or diluent.

In one embodiment, the warm-blooded animal is a mammalian species including, but not limited to, for example, humans and domestic animals, such as, for example, dogs, cats, and horses.

In a further embodiment, the warm-blooded animal is a human.

In one embodiment, the disease and/or condition for which a compound in accordance with formula I may be used in the treatment of or the prophylaxis of includes, but is not limited to, for example, mood disorders, anxiety disorders, and eating disorders.

Exemplary mood disorders include, but are not limited to, for example, depressive disorder(s), such as, for example, major depressive disorder(s) and dysthymic disorder(s); bipolar depression and/or bipolar mania, such as, for example, bipolar I, including but not limited to those with manic, depressive or mixed episodes, and bipolar II; cyclothymiac's disorder(s); anxious depression; and mood disorder(s) due to a general medical condition.

Exemplary anxiety disorder(s) include, but are not limited to, for example, panic disorder(s) without agoraphobia; panic disorder(s) with agoraphobia; agoraphobia without history of panic disorder(s); specific phobia; social phobia; obsessive-compulsive disorder(s); stress related disorder(s); posttraumatic stress disorder(s); acute stress disorder(s); generalized anxiety disorder(s); and generalized anxiety disorder(s) due to a general medical condition.

Exemplary eating disorders, include, but are not limited to, for example, obesity.

Many of the above conditions and disorder(s) are defined for example in the American Psychiatric Association: Diagnostic and Statistical Manual of Mental Disorders, Fourth Edition, Text Revision, Washington, D.C., American Psychiatric Association, 2000.

Another embodiment is directed to a method for treatment or prophylaxis of a mood disorder, anxiety disorder, or eating disorder comprising administering to a warm-blooded animal in need of such treatment or prophylaxis a therapeutically effective amount to of a compound according to formula I, or a pharmaceutically acceptable salt, thereof.

Yet another embodiment is directed to a method for treatment or prophylaxis of at least one mood disorder comprising administering to a warm-blooded animal in need of such treatment or prophylaxis a therapeutically effective amount of a compound according to formula I, or a pharmaceutically acceptable salt, thereof.

Still yet another embodiment is directed to a method for treatment or prophylaxis of at least one anxiety disorder comprising administering to a warn-blooded animal in need of such treatment or prophylaxis a therapeutically effective amount of a compound according to formula I, or a pharmaceutically acceptable salt thereof.

Still an even further embodiment is directed to a method for treatment or prophylaxis of at least one eating disorder comprising administering to a warm-blooded animal in need of such treatment or prophylaxis a therapeutically effective amount of a compound according to formula I, or a pharmaceutically acceptable salt thereof.

Another embodiment provides a method for treatment or prophylaxis of at least one disease or condition selected from anxiety, depression and obesity in a warm-blooded animal, comprising administering to said animal in need of such treatment or prophylaxis a therapeutically effective amount of a compound according to formula I.

Yet another embodiment provides a method for treatment or prophylaxis of anxiety in a warm-blooded animal, comprising administering to said animal in need of such treatment or prophylaxis a therapeutically effective amount of a compound according to formula I.

A further embodiment provides a method for treatment or prophylaxis of general anxiety disorder in a warm-blooded animal, comprising administering to said animal in need of such treatment or prophylaxis a therapeutically effective amount of a compound according to formula I.

Still yet another embodiment provides a method for treatment or prophylaxis of depression in a warm-blooded animal, comprising administering to said animal in need of such treatment or prophylaxis a therapeutically effective amount of a compound according to formula I.

Still yet an even further embodiment provides a method for treatment or prophylaxis of obesity in a warm-blooded animal, comprising administering to said animal in need of such treatment or prophylaxis a therapeutically effective amount of a compound according to formula I.

A more particular embodiment relates to a method for treatment or prophylaxis of a disease or condition in which modulation of the MCH1 receptor is beneficial comprising administering to a warm-blooded animal in need of such treatment or prophylaxis a therapeutically effective amount of an antagonistic compound of formula I.

A further embodiment is directed to a method for treatment or prophylaxis of a disease or condition selected from anxiety, depression and obesity in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of anxiety in a warm-blooded animal, comprising administering to said animal in need of such treatment or prophylaxis a therapeutically effective amount of a compound of formula I or a pharmaceutically-acceptable salt thereof.

Yet a further embodiment is directed to a method for treatment or prophylaxis of general anxiety disorder in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of depression in a warm-blooded animal, comprising administering to said animal in need of such treatment or prophylaxis a therapeutically effective amount of a compound of formula I or a pharmaceutically-acceptable salt thereof.

A further embodiment is directed to a method for treatment or prophylaxis of obesity in a warm-blooded animal, comprising administering to said animal in need of such treatment or prophylaxis a therapeutically effective amount of a compound of formula I or a pharmaceutically-acceptable salt thereof.

An even still further embodiment is directed to a compound of formula I, or a pharmaceutically acceptable salt thereof, for use in the treatment or prophylaxis of a disease or condition in which modulation of the MCH1 receptor is beneficial.

A more particular embodiment relates to an antagonistic-compound of formula I, or a pharmaceutically acceptable salt thereof, for use in the treatment or prophylaxis of a disease or condition in which modulation of the MCH1 receptor is beneficial.

A further embodiment is directed to a compound of formula I, or a pharmaceutically acceptable salt thereof for use in the treatment or prophylaxis of a disease or condition selected from mood disorder, anxiety disorder, and eating disorder.

A still further embodiment is directed to a compound of formula I, or a pharmaceutically acceptable salt thereof, for use in the treatment or prophylaxis of mood disorder.

An even further embodiment is directed to a compound of formula I, or a pharmaceutically acceptable salt thereof for use in the treatment or prophylaxis of anxiety disorder.

An even still further embodiment is directed to a compound of formula I, or a pharmaceutically acceptable salt thereof, for the treatment or prophylaxis of an eating disorder.

Yet a still further embodiment is directed to a compound of formula I, or a pharmaceutically acceptable salt thereof, for use in the treatment or prophylaxis of a disease or condition selected from anxiety, depression and obesity.

Still yet a further embodiment is directed to a compound of formula I, or a pharmaceutically acceptable salt thereof, for use in the treatment or prophylaxis of anxiety.

Yet still a further embodiment is directed to a compound of formula I, or a pharmaceutically acceptable salt thereof, for use in the treatment or prophylaxis of general anxiety disorder.

Even still yet a further embodiment is directed to a compound of formula I, or a pharmaceutically acceptable salt thereof, or mixtures thereof for use in the treatment or prophylaxis of depression.

Yet another embodiment is directed to a compound of formula I, or a pharmaceutically acceptable salt thereof, for use in the treatment or prophylaxis of obesity.

Yet a further embodiment is directed to the use of a compound of formula I, or a pharmaceutically acceptable salt thereof, in the manufacture of a medicament for the treatment or prophylaxis of a disease or condition in which modulation of the MCH1 receptor is beneficial.

A further embodiment is directed to the use of a compound of formula I, or a pharmaceutically acceptable salt thereof, in the manufacture of a medicament for the treatment or prophylaxis of a disease or condition selected from mood disorder, anxiety disorder, and eating disorder.

Yet a further embodiment is directed to using a compound of formula I, or a pharmaceutically acceptable salt thereof, in the manufacture of a medicament for the treatment or prophylaxis of mood disorder.

A still further embodiment is directed to using a compound of formula I, or a pharmaceutically acceptable salt thereof, in the manufacture of a medicament for the treatment or prophylaxis of anxiety disorder.

Still yet a further embodiment is directed to using a compound of formula I, or a pharmaceutically acceptable salt thereof, in the manufacture of a medicament for the treatment or prophylaxis of an eating disorder.

An even further embodiment is directed to using a compound of formula I, or a pharmaceutically acceptable salt thereof, in the manufacture of a medicament for the treatment or prophylaxis of a disease or condition selected from anxiety, depression and obesity.

A still even further embodiment is directed to using a compound of formula I, or a pharmaceutically acceptable salt thereof, in the manufacture of a medicament for the treatment or prophylaxis of anxiety.

A yet even further embodiment is directed to using a compound of formula I, or a pharmaceutically acceptable salt thereof, in the manufacture of a medicament for the treatment or prophylaxis of general anxiety disorder.

A yet still even further embodiment is directed to using a compound of formula I, or a pharmaceutically acceptable salt thereof, in the manufacture of a medicament for the treatment or prophylaxis of depression.

Another embodiment is directed to the use of a compound of formula I, or a pharmaceutically acceptable salt thereof, in the manufacture of a medicament for the treatment or prophylaxis of obesity.

A further embodiment is directed to using a compound of formula I, or a pharmaceutically acceptable salt thereof, for the treatment or prophylaxis insulin resistance, hepatic steatosis (including NASH), fatty liver, or sleep apnea.

Still yet a further embodiment is directed to using a compound of formula I, or a pharmaceutically acceptable salt thereof, as a medicament.

Another embodiment is directed to a pharmaceutical composition comprising a compound of formula I, or a pharmaceutically acceptable salt thereof, and a pharmaceutically acceptable carrier and/or diluent.

A further embodiment relates to a pharmaceutical composition useful for treatment or prophylaxis of a disease or condition mentioned herein arising from dysfunction of MCH1 receptors in a warm blooded animal comprising a therapeutically-effective amount of a compound of formula I, or a pharmaceutically-acceptable salt thereof, effective for treatment or prophylaxis of such disease or condition, and at least one pharmaceutically-acceptable carrier and/or diluent.

In one embodiment, the warm-blooded animal is a mammalian species including, but not limited to, for example, humans and domestic animals, such as, for example, dogs, cats, and horses.

In a further embodiment, the warm-blooded animal is a human.

Yet another embodiment provides at least one process for preparing a compound of Formula I.

In still yet another embodiment, a compound of formula I, or a pharmaceutically acceptable salt thereof, and/or a pharmaceutical composition or formulation comprising a compound of formula I, or a pharmaceutically acceptable salt thereof, may be administered concurrently, simultaneously, sequentially or separately with at least one other pharmaceutically active compound selected from the following:

(i) antidepressants, including, but not limited to, for example, agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine, and equivalents and pharmaceutically active isomer(s) and metabolite(s) thereof;

(ii) atypical antipsychotics including, but not limited to, for example, quetiapine, and pharmaceutically active isomer(s) and metabolite(s) thereof;

(iii) antipsychotics including, but not limited to, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and metabolite(s) thereof;

(iv) anxiolytics including, but not limited to, for example, alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydranine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam, and equivalents and pharmaceutically active isomer(s) and metabolite(s) thereof;

(v) anticonvulsants including, but not limited to, for example, carbamazepine, valproate, lamotrogine, gabapentin, and equivalents and pharmaceutically active isomer(s) and metabolite(s) thereof;

(vi) Alzheimer's therapies including, but not limited to, for example, donepezil, memantine, tacrine, and equivalents and pharmaceutically active isomer(s) and metabolite(s) thereof;

(vii) Parkinson's therapies including, but not limited to, for example, deprenyl, L-dopa, Requip, Mirapex, MAOB inhibitors such as selegeline and rasagiline, comP inhibitors such as Tasmar, A-2 inhibitors, dopamine reuptake inhibitors, NMDA antagonists, Nicotine agonists, Dopamine agonists, inhibitors of neuronal nitric oxide synthase, and equivalents and pharmaceutically active isomer(s) and metabolite(s) thereof:

(viii) migraine therapies including, but not limited to, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof (ix) stroke therapies including, but not limited to, for example, abciximab, activase, NXY-059, citicoline, crobenetine, desmoteplase, repinotan, traxoprodil, and equivalents and pharmaceutically active isomer(s) and metabolite(s) thereof;

(x) urinary incontinence therapies including, but not limited to, for example, darafenacin, falvoxate, oxybutynin, propiverine, robalzotan, solifenacin, tolterodine, and equivalents and pharmaceutically active isomer(s) and metabolite(s) thereof;

(xi) neuropathic pain therapies including, but not limited to, for example, gabapentin, lidoderm, pregablin, and equivalents and pharmaceutically active isomer(s) and metabolite(s) thereof;

(xii) nociceptive pain therapies including, but not limited to, for example, celecoxib, etoricoxib, lumiracoxib, rofecoxib, valdecoxib, diclofenac, loxoprofen, naproxen, paracetamol, and equivalents and pharmaceutically active isomer(s) and metabolite(s) thereof:

(xiii) insomnia therapies including, but not limited to, for example, agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem, and equivalents and pharmaceutically active isomer(s) and metabolite(s) thereof;

(xiv) mood stabilizers including, but not limited to, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof:

(xv) insulin or insulin analogues;

(xvi) insulin secretagogues including sulphonylureas (for example glibenclamide, glipizide), prandial glucose regulators (for example meglitindes e.g. repaglinide and nateglinide);

(xvii) dipeptidyl peptidase IV inhibitors (for example saxagliptin, sitagliptin, aloglitptin or vildagliptin);
(xviii) insulin sensitising agents including PPARgamma agonists (for example pioglitazone and rosiglitazone), and agents with combined PPARalpha and gamma activity;
(xix) agents that modulate hepatic glucose balance (for example biguanides e.g. metformin, fructose 1, 6 bisphosphatase inhibitors, glycogen phosphorylase inhibitors, glycogen synthase kinase inhibitors);
(xx) agents designed to reduce the absorption of glucose from the intestine (for example alpha glucosidase inhibitors e.g. acarbose);
(xxi) agents that prevent the reabsorption of glucose by the kidney (for example SGLT-2 inhibitors for example dapagliflozin or canagliflozin);
(xxii) agents designed to treat the complications of prolonged hyperglycaemia (for example aldose reductase inhibitors);
(xxiii) an anti-obesity compound, for example orlistat (EP 129 748) or sibutramine (GB 2,184,122 and U.S. Pat. No. 4,929,629);
(xxiv) anti-dyslipidaemia agents such as, HMG-CoA reductase inhibitors (eg statins for example rosuvastatin); PPARα agonists (fibrates, e.g. fenofibrate, clofibrate and gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
(xxv) antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
(xxvi) haemostasis modulators such as, antithrombotics, activators of fibrinolysis; thrombin antagonists; factor Xa inhibitors; factor VIIa inhibitors; antiplatelet agents (eg. aspirin, clopidogrel); anticoagulants (heparin and Low molecular weight analogues, hirudin) and warfarin;
(xxvii) agents which antagonise the actions of glucagon;
(xxviii) anti-inflammatory agents, such as non-steroidal anti-inflammatory drugs (eg. aspirin) and steroidal anti-inflammatory agents (eg. cortisone);
(xxix) an antihypertensive compound, for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, an AT-1 receptor blocker, a saluretic, a diuretic or a vasodilator;
(xxx) a PDK inhibitor;
(xxxi) a phytosterol compound;
(xxxii) an 11β HSD-1 inhibitor;
(xxxiii) an UCP-1, 2 or 3 activator;
(xxxiv) a CB1 receptor modulator for example an inverse agonist or an antagonist e.g. rimonabant or taranabant;
(xxxv) an NPY receptor modulator; for example an NPY agonist or an NPY2 agonist or an NPY5 antagonist;
(xxxvi) an MC4r modulator for example an MC4r agonist;
(xxxvii) an MC3r modulator for example an MC3r agonist;
(xxxviii) an orexin receptor modulator for example an antagonist;
(xxxix) modulators of nuclear receptors for example LXR, FXR, RXR, GR, ERRα, β, PPARα, β, γ, δ and RORalpha;
(xl) a DGAT1 inhibitor;
(xli) a DGAT2 inhibitor;
(xlii) a DGAT2 anti-sense oligonucleotide;
(xliii) a fatty acid synthase inhibitor
(xliv) a CETP (cholesteryl ester transfer protein) inhibitor;
(xlv) a cholesterol absorption antagonist;
(xlvi) a MTP (microsomal transfer protein) inhibitor;
(xlvii) probucol;
(xlviii) a GLP-1 agonist;
(xlix) a glucokinase modulator
l) a ghrelin antibody;
li) a ghrelin antagonist;
lii) a GPR119 agonist and
liii) another melanin concentrating hormone (MCH) modulator for example an MCH-1 antagonist;
or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

The above other pharmaceutically active compound, when employed in combination with the compounds of formula I, or pharmaceutically acceptable salts thereof, or mixtures thereof may be used, for example, in the amounts indicated in the Physicians' Desk Reference (PDR) or as otherwise determined by one of ordinary skill in the art.

For the uses, methods, medicaments and compositions mentioned herein the amount of formula I compound, or pharmaceutically acceptable salts thereof, or mixtures thereof used and the dosage administered may vary with the formula I compound, or pharmaceutically acceptable salts, or mixtures thereof employed; and/or the desired mode of administration and/or treatment. However, in general, satisfactory results are obtained when a compound in accordance with formula I, or pharmaceutically acceptable salts, or mixtures thereof is administered at a daily dosage of about 0.1 mg to about 20 mg/kg of animal body weight. Such doses may be given in divided doses 1 to 4 times a day or in a sustained release form. For man, the total daily dose may, for example, range of from about 5 mg to about 1,400 mg, and more particularly from about 10 mg to about 100 mg. Unit dosage forms suitable for oral administration generally comprise, for example, from about 2 mg to about 1,400 mg of at least one compound in accordance with formula I, or pharmaceutically acceptable salts, or mixtures thereof admixed with at least one solid and/or liquid pharmaceutical carrier, lubricant, and/or diluent.

The specific dose level and frequency of dosage for any particular subject, however, may vary and generally depends on a variety of factors, including, but not limited to, for example, the bioavailability of the specific formula I compound(s), or pharmaceutically acceptable salts, or mixtures thereof in the administered form; metabolic stability and length of action of the specific formula I compound(s), or pharmaceutically acceptable salts, or mixtures thereof; species, age, body weight, general health, sex, and diet of the subject; mode and time of administration; rate of excretion; drug combination; and severity of the particular condition.

Compound(s) in accordance with formula I, or pharmaceutically acceptable salts, or mixtures thereof may be administered by any means suitable for the condition to be treated and the quantity of formula I, or pharmaceutically acceptable salts, or mixtures thereof to be delivered.

Compound(s) in accordance with formula I, or pharmaceutically acceptable salts, or mixtures thereof may be administered in the form of a conventional pharmaceutical composition by any route including, but not limited to, for example, orally, intramuscularly, subcutaneously, topically, intranasally, epidurally, intraperitoneally, intrathoracially, intravenously, intrathecally, intracerebroventricularly, and injecting into the joints.

In one embodiment, the route of administration is orally, intravenously or intramuscularly.

A compound of formula I, or pharmaceutically acceptable salts, or mixtures thereof may be used on their own or in the form of appropriate medicinal preparations for enteral or parenteral administration.

Acceptable solid pharmaceutical compositions include, but are not limited to, for example, powders, tablets, dispersible granules, capsules, cachets, and suppositories.

In a solid pharmaceutical composition, pharmaceutically acceptable carriers include, but are not limited to, for example, at least one solid, at least one liquid, and mixtures thereof. The solid carrier can also be a diluent, flavoring agent, solubilizer, lubricant, suspending agent, binder, encapsulating material, and/or table disintegrating agent. Suitable carriers, include, but are not limited to, for example, magnesium carbonate; magnesium stearate; talc; lactose; sugar; pectin; dextrin; starch; tragacanth; methyl cellulose; sodium carboxymethyl cellulose; a low-melting wax; cocoa butter; and mixtures thereof.

A powder can be prepared by, for example, mixing a finely divided solid with at least one finely divided compound of formula I, or pharmaceutically acceptable salts, or mixtures thereof.

A tablet can be prepared by, for example, mixing at least one compound in accordance with formula I, or pharmaceutically acceptable salts, or mixtures thereof in suitable proportions with a pharmaceutically acceptable carrier having the necessary binding properties and compacted into the desired shape and size.

A suppository can be prepared by, for example, mixing at least one compound of formula I, or pharmaceutically acceptable salts, or mixtures thereof with at least one suitable non-irritating excipient that is liquid at rectal temperature but solid at a temperature below rectal temperature, wherein the non-irritating excipient is first melted and the formula I compound dispersed therein. The molten homogeneous mixture in then poured into convenient sized molds and allowed to cool and solidify. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Acceptable liquid pharmaceutical compositions include, but are not limited to, for example, solutions, suspensions, and emulsions.

Exemplary liquid pharmaceutical compositions suitable for parenteral administration include, but are not limited to, for example, sterile water or water propylene glycol solutions of at least one compound in accordance with formula I, or pharmaceutically acceptable salts, or mixtures thereof; and aqueous polyethylene glycol solutions of at least one compound in accordance with formula I, or pharmaceutically acceptable salts, or mixtures thereof.

Aqueous solutions for oral administration can be prepared by dissolving at least one compound in accordance with formula I, or pharmaceutically acceptable salts, or mixtures thereof in water and adding suitable colorants, flavoring agents, stabilizers, and/or thickening agents as desired.

Aqueous suspensions for oral administration can be prepared by dispersing at least one finely divided compound of formula I, or pharmaceutically acceptable salts, or mixtures thereof in water together with a viscous material, such as, for example, a natural synthetic gum, resin, methyl cellulose, and sodium carboxymethyl cellulose.

In one embodiment, the pharmaceutical composition contains from about 0.05% to about 99% w (percent by weight) of at least one compound in accordance with formula I, or pharmaceutically acceptable salts, or mixtures thereof. All percentages by weight are based on total composition.

In another embodiment, the pharmaceutical composition contains from about 0.10% to about 50% w (percent by weight) of at least one compound in accordance with formula I, or pharmaceutically acceptable salts, or mixtures thereof. All percentages by weight are based on total composition.

Also provided herein is a process for preparing a pharmaceutical composition comprising mixing or compounding the ingredients together and forming the mixed ingredients into tablets or suppositories; encapsulating the ingredients in capsules; or dissolving the ingredients to form injectable solutions.

Assay Methods:

MCH Binding Assay:

Binding of Melanin Concentrating Hormone (MCH) may be measured with a radioligand-binding assay employing $[^{125}I]$MCH and membranes expressing human Melanin Concentrating Hormone receptor 1 (MCHR1). Ligands that bind to MCHR1 may be identified by their ability to compete with the binding of $[^{125}I]$MCH.

$[^{125}I]$MCH may be purchased from Perkin Elmer (NEK373050UC 25 µCi). Membranes (2.20 mg/mL) may be prepared from CHOK1 cells expressing human MCH receptor 1 such as those obtainable from EuroScreen. Trizma, BSA, NaCl, and $MgCl_2 6H_2O$ may be purchased from Sigma. Human MCH may be purchased from Bachem (0.5 mg, cat # H-1482).

Saturation binding assays may be run in 50 mM Tris, pH 7.4, containing 3 mM $MgCl_2$ and 0.05% BSA. To perform an assay, 100 µL of 2-fold serially diluted radioligand $[^{125}I]$MCH is added to wells of a shallow 96-well plate. This is followed by addition of 100 µL of assay buffer containing membranes at a final protein concentration of 20 µg/mL. The mixture is incubated at room temperature for 1 h before being filtered through a Wallac A-filter treated with 0.1% PEI using a cell harvester (Skatron). Collected membranes are washed 3 times with 300 µL/well of wash buffer (50 mM Tris, pH 7.4, containing 5 mM $MgCl_2$ and 50 mM NaCl), and then dried in air overnight or at 60° C. $^{125}I$ is measured by scintillation counting.

$[^{125}I]$MCH binding assays performed in the presence of test compounds, either at fixed or a series of concentrations, may be employed in a ligand competition binding assay. For dose-response assays, compounds may be 3-fold serially diluted in an assay plate to produce a range of concentrations. For single point assays, $[^{125}I]$MCH and membranes may be pre-mixed and then transferred to an assay plates with respective final membrane protein and radioligand concentrations of 20 µg/mL and 0.04 nM.

For analysis of data from saturation binding, cpm are converted to dpm, and nM radioligand concentration is calculated using vendor-provided specific radioactivity.

Saturation binding data may be analyzed using equation (1):

$$B = \frac{B_{max}[[^{125}I]MCH]}{K_d + [[^{125}I]MCH]} \quad (1)$$

where B is concentration of bound ligand, $B_{max}$ is the maximum concentration of bound ligand, and $K_d$ is the dissociation constant for ligand.

Percent inhibition (% Inh) may be calculated using equation (2):

$$\% \ Inh = 100 \Big/ \left(1 - \frac{(counts_{sample} - counts_{negative})}{(counts_{positive} - counts_{negative})}\right) \quad (2)$$

IC$_{50}$ values may be calculated by conventional methods using non-linear squares analysis.

MCHR1 Receptor Activation Assay:

Melanin Concentrating Hormone Receptor 1 (MCHR1) is a G-protein coupled receptor that interacts with heterotrimeric G proteins containing a G$\alpha_{i/o}$ subunit. Binding of MCH to MCHR1 results in the exchange of GDP for GTP on the G$\alpha_{i/o}$ proteins associated with the activated receptor. This activation can be quantified by measuring the amount of a GTP analog, GTP$\gamma^{35}$S, bound to the membrane-associated receptor. GTP$\gamma^{35}$S is not hydrolyzed by the intrinsic GTPase activity of a G-protein but instead forms a stable complex. Activation of MCH1 receptors may thus be quantified by measuring the amount of GTP$\gamma^{35}$S bound to membranes prepared from cells expressing such receptors. Membranes may be isolated by filtration or may be bound on SPA beads (Amersham). Bound GTP$\gamma^{35}$S may then be quantified by determining the amount of $^{35}$S present. Inhibition of MCH binding by a competing ligand may thus be assessed by a decrease in the amount of GTP$\gamma^{35}$S bound to membranes in the presence of such a competing ligand.

Estimation of Covalent Binding of Small Molecules to Proteins in Hepatocytes:

The assay is based on the modification of a published method (Day, S. H.; Mao, A.; White, R.; Schulz-Utermoehl, T.; Miller, R.; Beconi, M. G. (2005) A semi-automated method for measuring the potential for protein covalent binding in drug discovery. *J. Pharmacol. Toxicol. Methods* 52, 278-285.). Briefly, cryopreserved human hepatocytes are incubated in the presence of radiolabeled drug candidate in 24-well plates for a pre-determined period to allow sufficient turnover of the parent compound. Following the incubation period, samples are taken out and quenched by cold acetone in order to facilitate precipitation of proteins. The precipitated protein samples are collected on glass fiber filter papers using a Brandel Harvester and washed with 80% methanol to remove non-covalently bound parent drug and metabolites. After solubilization of proteins collected on filter papers, radioactive content and amount of protein is determined to give an estimate of pmol equivalent drug molecule bound per mg protein. In addition to assessing the extent of covalent binding, the turnover of the parent drug is quantified to give an estimate of fraction of metabolites leading to covalent binding (f$_{CVB}$).

IC$_{50}$ Values

The compounds of the examples when tested in the above referenced assays had an IC$_{50}$ value of less than about 500 nM. The IC$_{50}$ values for the Example compounds are set forth in Table 1 hereinbelow.

TABLE 1

| Example No. | GTP$\gamma^{35}$S IC$_{50}$ (nM) |
| --- | --- |
| 1 | 18 |
| 2 | 11 |
| 3 | 13 |
| 4 | 16 |
| 5 | 19 |
| 6 | 19 |
| 7 | 20 |
| 8 | 20 |
| 9 | 15 |
| 10 | 18 |
| 11 | 15 |
| 12 | 45 |
| 13 | 70 |
| 14 | 23 |
| 15 | 58 |
| 16 | 34 |
| 17 | 420 |
| 18 | 150 |
| 19 | 38 |
| 22 | 23 |

Certain compounds of the invention are advantageous because they exhibit selectivity between their MCH activity and their hERG activity. Certain compounds of the invention are particularly advantageous because they are surprisingly more potent in vivo than might be expected from their in vitro activity and/or because they possess an advantageous metabolic profile. One aspect of the metabolic profile is the formation of reactive metabolites, where compounds of this invention in general are less prone to form such reactive metabolites. In vitro assessment of the formation of reactive metabolites can be made by measuring the degree of binding of a $^3$H- or $^{14}$C-labelled compound to human hepatocytes according to the method described above. An f$_{CVB}$ value can then be calculated. For instance, for Example 5 of this invention the f$_{CVB}$ value was found to be 0.0069, which can be compared to Example 4 described in WO 2010/125390 for which the f$_{CVB}$ value was calculated to 0.02 from experiments under the same assay conditions.

For a more complete assessment of the presence of reactive metabolites, the daily human dose prediction also has to be taken into account. The combined value calculated is known as covalent binding burden. (Reference: Thompson, R. et al *Chem. Res. Tox.* 2012 Published on the web: dx.doi.org/10.1021/tx300091x). Certain compounds of this invention differ from compounds previously described in WO2010/125390 in that a lower value covalent binding burden can be calculated from the combined assessment using both the predicted daily dose to man and the degree of covalent binding to human hepatocytes (f$_{CVB}$).

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In general, the compounds of Formula I can be prepared in accordance with the general knowledge of one skilled in the art and/or using methods set forth in the Example and/or Intermediate sections that follow. Solvents, temperatures, pressures, and other reaction conditions can readily be selected by one of ordinary skill in the art. Starting materials are commercially available and/or readily prepared by one skilled in the art. Combinatorial techniques can be employed in the preparation of compounds, for example, where the intermediates possess groups suitable for these techniques.

The following abbreviations are employed herein: ACN: acetonitrile; APCI: atmospheric pressure chemical ionization; aq.: aqueous; BOC: 1,1-dimethylethoxycarbonyl; $Cs_2CO_3$: cesium carbonate; DCM: dichloromethane; DIAD: diisopropylazodicarboxylate; DIBAL-H: diisobutylaluminium hydride; DIPEA: N,N-diisopropylethylamine; DMSO: dimethyl sulfoxide; EDCI: 1-(3-Dimethylaminopropyl)-3-ethylcarbodiimide hydrochloride; $Et_2O$: diethyl ether; EtOAc: ethyl acetate; EtOH: ethanol; h: hour(s); HPLC: high performance liquid chromatography; HCl: hydrochloric acid where a molarity is given or hydrogen chloride gas when a solvent other than water is used; $H_2O$: water; $K_2CO_3$: potassium carbonate; LC: liquid chromatography; MeOH: methanol; $MgSO_4$: magnesium sulfate; min: minutes; MS: mass spectrum; NaCl: Sodium chloride; $NH_4Cl$: ammonia hydrochloride; $NaHCO_3$: sodium bicarbonate; $Na_2SO_4$: Sodium sulfate; $NH_3$: Ammonia; NMR: nuclear magnetic resonance; psi: pounds per square inch; RT: room temperature; sat.: saturated; TBTU: 2-(1H-benzo[d][1,2,3]triazol-1-yl)-1,1,3,3-tetramethylisouronium tetrafluoroborate; TEA: triethylamine; TFA: trifluoroacetic acid; and THF: tetrahydrofuran.

Analytical LC/MS HPLC Method: Waters Acquity UPLC Column Acquity UPLC BEH C18, 1.7 um, 2.1×100 mm. Gradient 5-95% acetonitrile in ammonium carbonate buffer at pH10 (40 mM $NH_3$+6.5 mM $H_2CO_3$) in 5.8 minutes at 60° C. Flow 0.8 mL/min.

Preparative HPLC Method: Preparative HPLC was used routinely to separate the exemplified compounds. Instrument: FractionLynx I Mobilphase: gradient 5-95% ACN in 0.2% NH3 at pH10 Column: Xbridge Prep C18, 5 μm OBD 19*150 mm.

Chemical IUPAC names were generated by software provided by CambridgeSoft Corporation, Cambridge, Mass. 02140, USA.

Amines of formula IV are commercially available.

Example 1

(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone

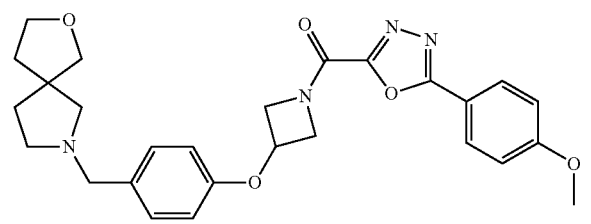 [SMILES: COc1ccc(-c2nnc(C(=O)N3CC(Oc4ccc(CN5CCC6(CCOC6)C5)cc4)C3)o2)cc1]

2-Oxa-7-azaspiro[4.4]nonane HCl salt (0.057 g, 0.35 mmol) was dissolved in dichloromethane (2 ml). To the resulting solution was added triethylamine (0.052 ml, 0.38 mmol), followed by 4-(1-(5-(4-methoxyphenyl)-1,3,4-oxadiazole-2-carbonyl)azetidin-3-yloxy)benzaldehyde (0.11 g, 0.29 mmol) and sodium triacetoxyhydroborate (0.123 g, 0.58 mmol). The mixture was stirred at ambient temperature overnight. The reaction mixture was then diluted with dichloromethane (10 ml) and shaken with $NaHCO_3$ (sat. 2 ml). The two phases were separated using a phase separator. The organic phase was evaporated. The product was purified by preparative reverse-phase HPLC at pH 10 to give 0.066 g (46%) of the desired product as a solid. $^1$H NMR (400 MHz, $CDCl_3$) δ 1.92 (ddd 4H), 2.42 (d, 1H), 2.62 (dd, 3H), 3.58 (d, 3H), 3.71 (d, 1H), 3.84 (ddd, 2H), 3.92 (s, 3H), 4.35 (d, 1H), 4.67 (dd, 1H), 4.77 (d, 1H), 5.04-5.19 (m, 2H), 6.75 (d, 2H), 7.05 (d, 2H), 7.29 (d, 2H), 8.12 (d, 2H). MS (APCI+) m/z 491.3 [M+H]$^+$, LC purity: 97%

It will be appreciated by one skilled in the art that the title compound is chiral. The individual enantiomers:

(+)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone and (−)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone were obtained by chiral chromatography on a Chiralpak® IA column (supplied by Chiral Technologies Europe) using a mobile phase comprising heptane/THF/triethylamine 60/40/0.1.

Example 2

(+/−)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone

ISOMER 1

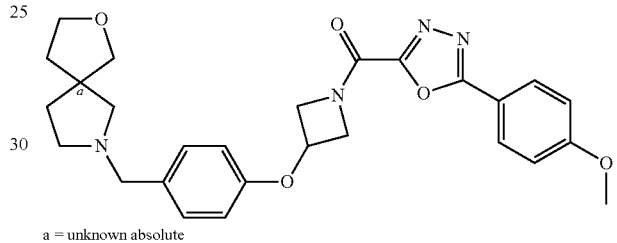

a = unknown absolute (3-(4-(2-Oxa-7-azaspiro[4.4]nonan-7-ylmethyl)phenoxy)azetidin-1-yl)(5-(4-methoxyphenyl)-1,3,4-oxadiazol-2-yl)methanone (isomer 1 from chiral LC separation) was further purified by column chromatography (ISOLUTE SI, 10/70 ml), eluting with $NH_3$ in MeOH (2M)/DCM (2:98) to afford 3 mg (2%) after evaporation of the solvent mixture. Optical rotation unknown. $^1$H NMR (400 MHz, $CDCl_3$): δ 1.77-1.99 (m, 4H), 2.39 (d, 1H), 2.53-2.69 (m, 3H), 3.5-3.6 (m, 3H), 3.69 (d, 1H), 3.75-3.87 (m, 2H), 3.89 (s, 3H), 4.33 (dd, 1H), 4.6-4.68 (m, 1H), 4.71-4.78 (m, 1H), 5.02-5.16 (m, 2H), 6.72 (d, 2H), 6.99-7.05 (m, 2H), 7.25 (d, 2H), 8.07-8.13 (m, 2H). MS (APCI+) m/z 491.3 [M+H]$^+$, LC purity: 99%

Example 3

(+/−)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone

ISOMER 2

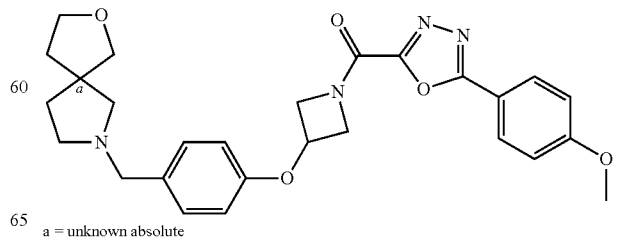

a = unknown absolute (3-(4-(2-Oxa-7-azaspiro[4.4]nonan-7-ylmethyl)phenoxy)azetidin-1-yl)(5-(4-methoxyphenyl)-1,3,4-oxadiazol-2-yl)methanone (isomer 2 from chiral LC separation) was further purified by column chromatography (ISOLUTE SI, 10/70 ml), eluting with NH$_3$ in MeOH (2M)/DCM (2:98) to afford 3 mg (2%) after evaporation of the solvent mixture. Optical rotation unknown. $^1$H NMR (400 MHz, CDCl$_3$): δ 1.77-1.98 (m, 4H), 2.39 (d, 1H), 2.52-2.7 (m, 3H), 3.49-3.6 (m, 3H), 3.68 (d, 1H), 3.75-3.87 (m, 2H), 3.88 (d, 3H), 4.33 (dd, 1H), 4.6-4.68 (m, 1H), 4.7-4.79 (m, 1H), 5.01-5.15 (m, 2H), 6.72 (d, 2H), 6.98-7.05 (m, 2H), 7.26 (d, 2H), 8.06-8.12 (m, 2H). MS (APCI+) m/z 491.3 [M+H]$^+$, LC purity: 99%.

Example 4

(3-(4-(5-oxa-2-azaspiro[3.4]octan-2-ylmethyl)phenoxy)azetidin-1-yl)(5-(4-methoxyphenyl)-1,3,4-oxadiazol-2-yl)methanone

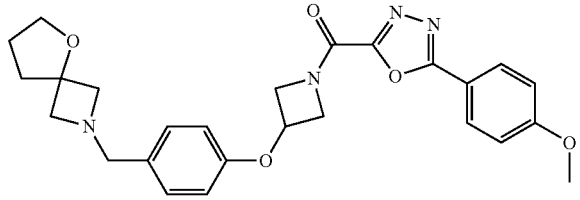 [SMILES: COc1ccc(-c2nnc(C(=O)N3CC(Oc4ccc(CN5CC6(CCCO6)C5)cc4)C3)o2)cc1]

5-Oxa-2-azaspiro[3.4]octane HCl salt (0.052 g, 0.35 mmol) was dissolved in dichloromethane (2 ml). Triethylamine (0.052 ml, 0.38 mmol) was added, followed by 4-(1-(5-(4-methoxyphenyl)-1,3,4-oxadiazole-2-carbonyl)azetidin-3-yloxy)benzaldehyde (0.11 g, 0.29 mmol) and finally sodium triacetoxyhydroborate (0.123 g, 0.58 mmol). The reaction was stirred at ambient temperature overnight. The reaction mixture was then diluted with dichloromethane (10 ml) and subsequently shaken with NaHCO$_3$ (sat. 2 ml). The two phases were separated using a phase separator. The organic phase was evaporated. The product was purified by preparative reverse-phase HPLC at pH 10 to give 23 mg (17%) of the desired product as a solid. $^1$H NMR (500 MHz, CDCl$_3$): δ 1.90 (p, 2H), 2.13 (t, 2H), 3.16 (d, 2H), 3.37 (d, 2H), 3.62 (s, 2H), 3.80 (t, 2H), 3.91 (s, 3H), 4.33 (dd, 1H), 4.62-4.7 (m, 1H), 4.73-4.78 (m, 1H), 5.03-5.16 (m, 2H), 6.74 (d, 2H), 7.04 (d, 2H), 7.25 (d, 2H), 8.11 (d, 2H). MS (APCI+) m/z 477.3 [M+H]$^+$, LC purity: 97%

Example 5

(3-(4-(6-oxa-2-azaspiro[3.4]octan-2-ylmethyl)phenoxy)azetidin-1-yl)(5-(4-methoxyphenyl)-1,3,4-oxadiazol-2-yl)methanone 6-Oxa-2-azaspiro[3.4]octane HCl salt (0.052 g, 0.35 mmol) was dissolved in dichloromethane (2 ml). Triethylamine (0.052 ml, 0.38 mmol) was added, followed by 4-(1-(5-(4-methoxyphenyl)-1,3,4-oxadiazole-2-carbonyl)azetidin-3-yloxy)benzaldehyde (0.11 g, 0.29 mmol) and then sodium triacetoxyhydroborate (0.123 g, 0.58 mmol). The reaction was stirred at ambient temperature overnight. The reaction mixture was then diluted with dichloromethane (10 ml), after which it was shaken with NaHCO$_3$ (sat. 2 ml).

The two phases were separated by the use of a phase separator. Evaporation of dichloromethane afforded crude material, which was purified by preparative reverse-phase HPLC at pH 10 to give 59 mg (43%) of the desired product as a solid. $^1$H NMR (400 MHz, CDCl$_3$): δ 2.12 (t, 2H), 3.24 (s, 4H), 3.58 (s, 2H), 3.79 (t, 2H), 3.85 (s, 2H), 3.92 (s, 3H), 4.34 (dd, 1H), 4.66 (dd, 1H), 4.76 (d, 1H), 5.04-5.18 (m, 2H), 6.75 (d, 2H), 7.05 (d, 2H), 7.25 (d, 2H), 8.12 (d, 2H). MS (APCI+) m/z 477.3 [M+H]$^+$, LC purity: 96%.

Example 6

(3-(4-(2-oxa-7-azaspiro[4.4]nonan-7-ylmethyl)phenoxy)azetidin-1-yl)(5-phenyl-1,3,4-oxadiazol-2-yl)methanone

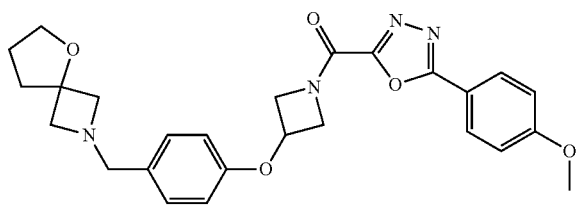

To a solution of 4-(1-(5-phenyl-1,3,4-oxadiazole-2-carbonyl)azetidin-3-yloxy)benzaldehyde (70 mg, 0.20 mmol) in dichloromethane (2 mL) was added triethylamine (0.100 mL, 0.72 mmol) and 2-oxa-7-azaspiro[4.4]nonane hydrochloride (77 mg, 0.47 mmol). The resulting mixture was stirred for 30 minutes at ambient temperature, after which was added sodium triacetoxyhydroborate (114 mg, 0.54 mmol). Stirring was continued at ambient temperature overnight, after which NaHCO$_3$ (aq, sat, 5 ml) was added to the reaction mixture. The phases were separated using a phase separator. The aqueous phase was extracted twice with dichloromethane and dried with the aid of a phase separator. The combined organic phases were concentrated in vacuo to afford a colourless residue weighing 112 mg. The crude material was purified by preparative reverse-phase HPLC at pH 10 to give 75 mg (81%) of the desired product as a solid. $^1$H NMR (600 MHz, CDCl$_3$): δ 1.75 (t, 2H), 1.79-1.89 (m, 2H), 2.32 (d, 1H), 2.45-2.49 (m, 2H), 2.59 (dd, 1H), 3.43 (d, 1H), 3.48-3.56 (m, 3H), 3.63-3.75 (m, 2H), 4.10 (dd, 1H), 4.56 (dd, 1H), 4.61-4.67 (m, 1H), 5.10 (dd, 1H), 5.16 (ddd, 1H), 6.86 (d, 2H), 7.26 (d, 2H), 7.63-7.73 (m, 3H), 8.06-8.11 (m, 2H). MS (APCI+) m/z 461.2 [M+H]$^+$, LC purity: 97%

It will be appreciated by one skilled in the art that the title compound is chiral. The individual enantiomers:

(+)-(3-(4-(2-oxa-7-azaspiro[4.4]nonan-7-ylmethyl)phenoxy)azetidin-1-yl)(5-phenyl-1,3,4-oxadiazol-2-yl)methanone and (−)-(3-(4-(2-oxa-7-azaspiro[4.4]nonan-7-ylmethyl)phenoxy)azetidin-1-yl)(5-phenyl-1,3,4-oxadiazol-2-yl)methanone may be obtained by chiral chromatography.

Example 7

(3-(4-(6-oxa-2-azaspiro[3.4]octan-2-ylmethyl)phenoxy)azetidin-1-yl)(5-phenyl-1,3,4-oxadiazol-2-yl)methanone

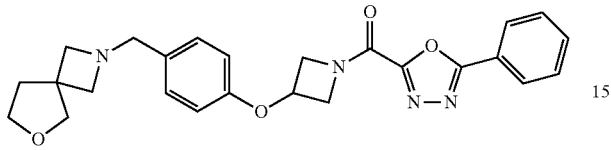

To a solution of 4-(1-(5-phenyl-1,3,4-oxadiazole-2-carbonyl)azetidin-3-yloxy)benzaldehyde (70 mg, 0.20 mmol) in dichloromethane (2 mL) was added 6-oxa-2-azaspiro[3.4]octane hydrochloride (56 mg, 0.37 mmol) and triethylamine (0.100 mL, 0.72 mmol). After stirring at ambient temperature for 30 minutes, sodium triacetoxyhydroborate (95 mg, 0.45 mmol) was added. Stirring was continued at ambient temperature overnight, after which NaHCO$_3$ (aq, sat, 5 ml) was added. The phases were separated with the aid of a phase separator. The aqueous phase was extracted twice with dichloromethane and dried using a phase separator. The combined organic phases were concentrated in vacuo to afford a colourless residue weighing 92 mg.

The crude material was purified by preparative reverse-phase HPLC at pH 10 to give 63 mg (71%) of the desired product as a solid. $^1$H NMR (600 MHz, DMSO) δ 2.00 (t, 2H), 3.11 (q, 4H), 3.49 (s, 2H), 3.64 (t, 2H), 3.69 (s, 2H), 4.07-4.11 (m, 1H), 4.55 (ddd, 1H), 4.63 (ddd, 1H), 5.07-5.17 (m, 2H), 6.82-6.86 (m, 2H), 7.23 (d, 2H), 7.63-7.72 (m, 3H), 8.06-8.1 (m, 2H). MS (APCI+) m/z 447.2 [M+H]$^+$, LC purity: 98%

Example 8

(3-(4-(5-oxa-2-azaspiro[3.4]octan-2-ylmethyl)phenoxy)azetidin-1-yl)(5-phenyl-1,3,4-oxadiazol-2-yl)methanone

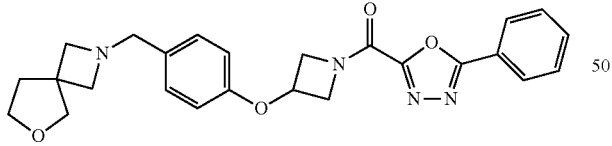

To a solution of 4-(1-(5-phenyl-1,3,4-oxadiazole-2-carbonyl)azetidin-3-yloxy)benzaldehyde (70 mg, 0.20 mmol) in dichloromethane (2 mL) was added 5-oxa-2-azaspiro[3.4]octane hydrochloride (80 mg, 0.53 mmol) and triethylamine (0.100 mL, 0.72 mmol). After stirring at ambient temperature for 30 minutes, sodium triacetoxyhydroborate (70 mg, 0.33 mmol) was added. Stirring was continued at ambient temperature overnight, after which NaHCO$_3$ (aq, sat, 5 ml) was added. The phases were separated with the aid of a phase separator. The aqueous phase was extracted twice with dichloromethane and dried with the aid of a phase separator. The combined organic phases were concentrated in vacuo to afford 88 mg of a colourless residue.

The crude material was purified by preparative reverse-phase HPLC at pH 10 to give 68 mg (76%) of the desired product as a solid. $^1$H NMR (600 MHz, DMSO) δ 1.80 (p, 2H), 2.00 (t, 2H), 2.98 (d, 2H), 3.22 (dd, 2H), 3.51 (s, 2H), 3.65 (q, 2H), 4.09 (ddd, 1H), 4.53-4.57 (m, 1H), 4.63 (ddd, 1H), 5.10 (ddd, 1H), 5.15 (ddd, 1H), 6.84 (t, 2H), 7.23 (d, 2H), 7.68 (dtd, 3H), 8.08 (dd, 2H). MS (APCI+) m/z 447.2 [M+H]$^+$, LC purity: 99%

Example 9

(3-(4-(6-oxa-2-azaspiro[3.4]octan-2-ylmethyl)-3-methylphenoxy)azetidin-1-yl)(5-phenyl-1,3,4-oxadiazol-2-yl)methanone

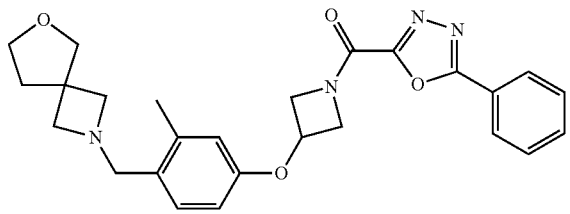

6-Oxa-2-azaspiro[3.4]octane HCl salt (0.064 g, 0.43 mmol) was dissolved in dichloromethane (2 ml). Triethylamine (0.064 ml, 0.47 mmol) was added, followed by 2-methyl-4-(1-(5-phenyl-1,3,4-oxadiazole-2-carbonyl)azetidin-3-yloxy)benzaldehyde (0.13 g, 0.36 mmol) and sodium triacetoxyhydroborate (0.152 g, 0.72 mmol). The mixture was stirred at ambient temperature overnight. The reaction mixture was diluted with dichloromethane (10 ml) and then shaken with NaHCO$_3$. The two phases were separated by the use of a phase separator. Evaporation of dichloromethane afforded crude material, which was purified by preparative reverse-phase HPLC at pH 10 to give 66 mg (40%) of the desired product as a solid. $^1$H NMR (600 MHz, DMSO) δ 2.01 (t, 2H), 2.27 (s, 3H), 3.13 (q, 4H), 3.47 (s, 2H), 3.64 (t, 2H), 3.70 (d, 2H), 4.08 (dd, 1H), 4.51-4.56 (m, 1H), 4.63 (dd, 1H), 5.06-5.15 (m, 2H), 6.65 (dd, 1H), 6.71 (d, 1H), 7.18 (d, 1H), 7.62-7.73 (m, 3H), 8.06-8.11 (m, 2H). MS (APCI+) m/z 461.2 [M+H]$^+$, LC purity: 98%

Example 10

(3-(4-(2-oxa-7-azaspiro[4.4]nonan-7-ylmethyl)-3-methylphenoxy)azetidin-1-yl)(5-phenyl-1,3,4-oxadiazol-2-yl)methanone

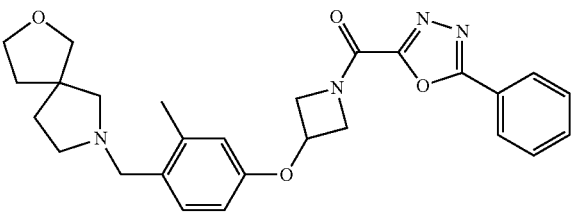 [SMILES: Cc1cc(OC2CN(C(=O)c3nnc(-c4ccccc4)o3)C2)ccc1CN1CCC2(CCOC2)C1]

2-Oxa-7-azaspiro[4.4]nonane HCl salt (0.07 g, 0.43 mmol) was dissolved in dichloromethane (2 ml). Triethylamine (0.064 ml, 0.47 mmol) was added, followed by 2-methyl-4-(1-(5-phenyl-1,3,4-oxadiazole-2-carbonyl)azetidin- 3-yloxy)benzaldehyde (0.13 g, 0.36 mmol) and sodium triacetoxyhydroborate (0.152 g, 0.72 mmol). The resulting mixture was stirred at ambient temperature overnight. The reaction mixture was diluted with dichloromethane (10 ml) and then shaken with NaHCO₃ (sat. 3 ml). The two phases were separated by the use of a phase separator. Evaporation of the organic phase afforded crude material, which was purified by preparative reverse-phase HPLC at pH 10 to give 85 mg (50%) of the desired product as a solid.

¹H NMR (600 MHz, DMSO) δ 1.76 (t, 2H), 1.78-1.89 (m, 2H), 2.32 (d, 4H), 2.47 (d, 2H), 2.57-2.61 (m, 1H), 3.41 (d, 1H), 3.45-3.54 (m, 3H), 3.65-3.74 (m, 2H), 4.09 (dd, 1H), 4.54 (dd, 1H), 4.61-4.66 (m, 1H), 5.12 (dtd, 2H), 6.66 (dd, 1H), 6.72 (d, 1H), 7.18 (d, 1H), 7.63-7.73 (m, 3H), 8.08 (dd, 2H). MS (APCI+) m/z 475.2 [M+H]⁺, LC purity: 98%. It will be appreciated by one skilled in the art that the title compound is chiral. The individual enantiomers:

(+)-(3-(4-(2-oxa-7-azaspiro[4.4]nonan-7-ylmethyl)-3-methylphenoxy)azetidin-1-yl)(5-phenyl-1,3,4-oxadiazol-2-yl)methanone and (−)-(3-(4-(2-oxa-7-azaspiro[4.4]nonan-7-ylmethyl)-3-methylphenoxy)azetidin-1-yl)(5-phenyl-1,3,4-oxadiazol-2-yl)methanone may be obtained by chiral chromatography Example 11

(3-(4-(5-oxa-2-azaspiro[3.4]octan-2-ylmethyl)-3-methylphenoxy)azetidin-1-yl)(5-phenyl-1,3,4-oxadiazol-2-yl)methanone

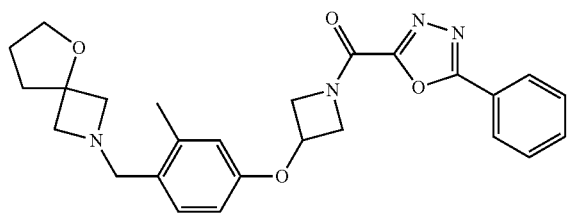 [SMILES: Cc1cc(OC2CN(C(=O)c3nnc(-c4ccccc4)o3)C2)ccc1CN1CC2(CCCO2)C1]

5-Oxa-2-azaspiro[3.4]octane HCl salt (0.064 g, 0.43 mmol) was dissolved in dichloromethane (2 ml). Triethylamime (0.064 ml, 0.47 mmol) was added, followed by 2-methyl-4-(1-(5-phenyl-1,3,4-oxadiazole-2-carbonyl)azetidin-3-yloxy)benzaldehyde (0.13 g, 0.36 mmol) and finally sodium triacetoxyhydroborate (0.152 g, 0.72 mmol). The resulting mixture was stirred at ambient temperature overnight. The reaction mixture was the diluted with dichloromethane (10 ml) and shaken with NaHCO₃ (sat. 3 ml). The two phases were separated by the use of a phase separator. Evaporation of the organic phase afforded a solid residue, which again was dissolved in dichloromethane (ca. 20 ml), washed with water (20 ml), filtered through a phase separator and evaporated. The residue was purified by column chromatography (ISOLUTE SI, 20 g/70 ml), eluting with NH₃ in MeOH (2M)/dichloromethane (1:99, 2:98). After evaporation of the solvent mixture, 112 mg (68%) of the desired product was obtained as a solid. ¹H NMR (400 MHz, CDCl₃) δ 1.91 (p, 2H), 2.14 (t, 2H), 2.33 (s, 3H), 3.15 (d, 2H), 3.39 (d, 2H), 3.59 (s, 2H), 3.82 (t, 2H), 4.35 (dd, 1H), 4.67 (dd, 1H), 4.74-4.8 (m, 1H), 5.11 (ddt, 2H), 6.57 (dd, 1H), 6.62 (d, 1H), 7.22 (d, 1H), 7.53-7.65 (m, 3H), 8.16-8.23 (m, 2H). MS (APCI+) m/z 461.3 [M+H]⁺, LC purity: 99%

Example 12

(3-(4-(2-oxa-5-azaspiro[3.4]octan-5-ylmethyl)phenoxy)azetidin-1-yl)(5-(4-methoxyphenyl)-1,3,4-oxadiazol-2-yl)methanone

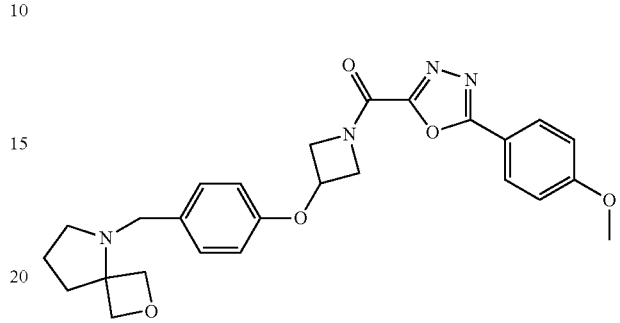

2-Oxa-5-azaspiro[3.4]octane (0.03 g, 0.26 mmol) was dissolved in dichloromethane (2 ml). Triethylamine (0.04 ml, 0.29 mmol) was added, followed by 4-(1-(5-(4-methoxyphenyl)-1,3,4-oxadiazole-2-carbonyl)azetidin-3-yloxy)benzaldehyde (0.1 g, 0.26 mmol) and finally sodium triacetoxyhydroborate (0.112 g, 0.53 mmol). The mixture was stirred at ambient temperature overnight. The reaction mixture was then diluted with dichloromethane (10 ml) and subsequently shaken with NaHCO₃ (sat. 3 ml). The two phases were separated by the use of a phase separator. Evaporation of the organic phase afforded a residue, which was purified by preparative reverse-phase. HPLC at pH 10 to give 0.075 g (60%) of the desired product as a solid. ¹H NMR (600 MHz, DMSO) δ 1.62 (dt, 2H), 2.1-2.15 (m, 2H), 2.49 (t, 2H), 3.88 (s, 3H), 3.91 (s, 2H), 4.09 (ddd, 1H), 4.43 (d, 2H), 4.54 (ddd, 1H), 4.63 (ddd, 1H), 4.80 (d, 2H), 5.09 (ddd, 1H), 5.16 (ddd, 1H), 6.86 (d, 2H), 7.17-7.21 (m, 2H), 7.30 (d, 2H), 8-8.04 (m, 2H). MS (APCI+) m/z 477.2 [M+H]⁺, LC purity: 95%

Example 13

(3-(4-(2-oxa-5-azaspiro[3.4]octan-5-ylmethyl)phenoxy)azetidin-1-yl)(5-phenyl-1,3,4-oxadiazol-2-yl)methanone

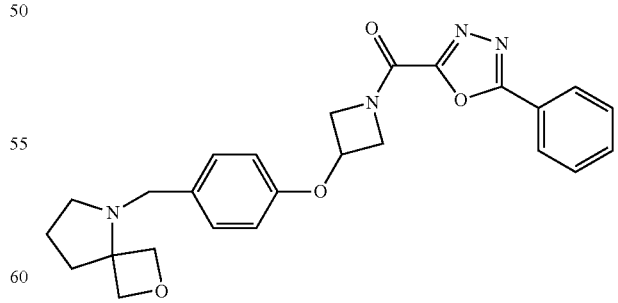

2-Oxa-5-azaspiro[3.4]octane TFA salt (0.16 g, 67%, 0.47 mmol) was dissolved in dichloromethane (3 ml). Triethyl amine (0.119 ml, 0.86 mmol) was added, followed by 4-(1-(5-phenyl-1,3,4-oxadiazole-2-carbonyl)azetidin-3-yloxy) benzaldehyde (0.15 g, 0.43 mmol) and finally sodium triacetoxyhydroborate (0.182 g, 0.86 mmol). The mixture was stirred at ambient temperature overnight. The reaction mixture was then diluted with dichloromethane (10 ml) was added and shaken with NaHCO₃ (sat. 3 ml). The two phases were separated by the use of a phase separator. Evaporation of the organic phase afforded a colourless residue, which was purified by preparative reverse-phase HPLC at pH 10 to give 0.140 g (73%) of the desired product as a solid. ¹H NMR (600 MHz, DMSO) δ 1.62 (dt, 2H), 2.09-2.15 (m, 2H), 2.47-2.5 (m, 2H), 3.90 (d, 2H), 4.08-4.14 (m, 1H), 4.43 (d, 2H), 4.54-4.59 (min, 1H), 4.64 (ddd, 1H), 4.80 (d, 2H), 5.09-5.13 (m, 1H), 5.16 (ddd, 1H), 6.87 (d, 2H), 7.30 (d, 2H), 7.64-7.74 (m, 3H), 8.07-8.13 (m, 2H). MS (APCI+) m/z 447.2 [M+H]⁺, LC purity: 94%.

Example 14

(3-(4-(7-oxa-1-azaspiro[4.4]nonan-1-ylmethyl)phenoxy)azetidin-1-yl)(5-(4-methoxyphenyl)-1,3,4-oxadiazol-2-yl)methanone

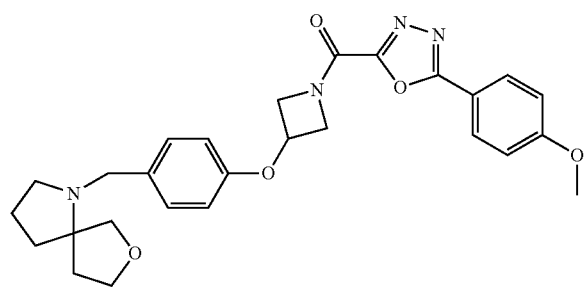 [SMILES: COc1ccc(-c2nnc(C(=O)N3CC(Oc4ccc(CN5CCCC56CCOC6)cc4)C3)o2)cc1]

7-Oxa-1-azaspiro[4.4]nonane TFA salt (0.07 g, 0.29 mmol) was dissolved in dichloromethane (2 ml). Triethylamine (0.044 ml, 0.32 mmol) was added, followed by 4-(1-(5-(4-methoxyphenyl)-1,3,4-oxadiazole-2-carbonyl)azetidin-3-yloxy)benzaldehyde (0.11 g, 0.29 mmol) and finally sodium triacetoxyhydroborate (0.123 g, 0.58 mmol). The mixture was stirred at ambient temperature overnight. The reaction mixture was then diluted with dichloromethane (10 ml) and shaken with NaHCO₃ (sat. 3 ml). The two phases were separated by the use of a phase separator. Evaporation of the organic phase afforded a residue, which was purified by preparative reverse-phase HPLC at pH 10 to give 0.072 g (51%) of the desired product as a solid. ¹H NMR (600 MHz, DMSO) δ 1.62-1.74 (m, 3H), 1.79-1.9 (m, 2H), 2.10 (dd, 1H), 2.42 (dd, 1H), 2.53-2.55 (m, 1H), 3.41 (d, 1H), 3.48 (d, 1H), 3.63 (d, 1H), 3.69 (q, 1H), 3.80 (d, 1H), 3.88 (s, 3H), 3.91 (td, 1H), 4.09 (dd, 1H), 4.54 (dd, 1H), 4.62 (ddd, 1H), 5.08 (ddd, 1H), 5.15 (ddd, 1H), 6.84 (d, 2H), 7.17-7.21 (m, 2H), 7.25 (d, 2H), 8-8.05 (m, 2H). MS (APCI+) m/z 491.2 [M+H]⁺, LC purity: 96%

It will be appreciated by one skilled in the art that the title compound is chiral. The individual enantiomers (+)-(3-(4-(7-oxa-1-azaspiro[4.4]nonan-1-ylmethyl)phenoxy)azetidin-1-yl)(5-(4-methoxyphenyl)-1,3,4-oxadiazol-2-yl)methanone and (−)-(3-(4-(7-oxa-1-azaspiro[4.4]nonan-1-ylmethyl)phenoxy)azetidin-1-yl)(5-(4-methoxyphenyl)-1,3,4-oxadiazol-2-yl)methanone may be obtained by chiral chromatography.

Example 15

(3-(4-(7-oxa-1-azaspiro[4.4]nonan-1-ylmethyl)phenoxy)azetidin-1-yl)(5-phenyl-1,3,4-oxadiazol-2-yl)methanone

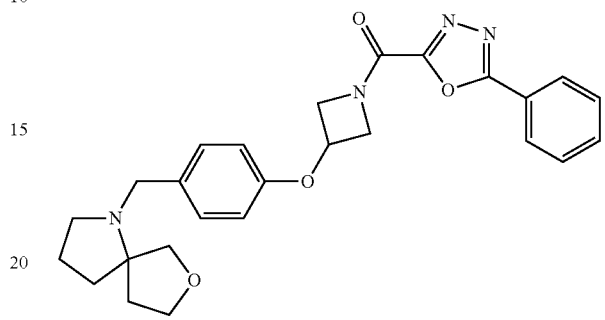

7-Oxa-1-azaspiro[4.4]nonane TFA salt (0.07 g, 0.29 mmol) was dissolved in dichloromethane (2 ml). Triethylamine (0.044 ml, 0.32 mmol) was added, followed by 4-(1-(5-phenyl-1,3,4-oxadiazole-2-carbonyl)azetidin-3-yloxy)benzaldehyde (0.101 g, 0.29 mmol) and finally sodium triacetoxyhydroborate (0.123 g, 0.58 mmol. The reaction mixture was then diluted with dichloromethane (10 ml) and shaken with NaHCO₃ (sat. 3 ml). The two phases were separated by the use of a phase separator. Evaporation of the organic phase afforded a residue, which was purified by preparative reverse-phase HPLC at pH 10 to give 0.081 g (61%) of the desired product as a solid. ¹H NMR (600 MHz, DMSO) δ 1.62-1.74 (m, 3H), 1.79-1.9 (m, 2H), 2.10 (dt, 1H), 2.37-2.45 (m, 1H), 2.54 (dd, 1H), 3.41 (d, 1H), 3.48 (d, 1H), 3.63 (d, 1H), 3.69 (q, 1H), 3.80 (d, 1H), 3.91 (td, 1H), 4.10 (dd, 1H), 4.56 (dd, 1H), 4.63 (ddd, 1H), 5.07-5.18 (m, 2H), 6.84 (d, 2H), 7.25 (d, 2H), 7.64-7.73 (m, 3H), 8.08 (dd, 2H). MS (APCI+) m/z 461.2 [M+H]⁺, LC purity: 97%

It will be appreciated by one skilled in the art that the title compound is chiral. The individual enantiomers (+)-(3-(4-(7-oxa-1-azaspiro[4.4]nonan-1-ylmethyl)phenoxy)azetidin-1-yl)(5-phenyl-1,3,4-oxadiazol-2-yl)methanone and (−)-(3-(4-(7-oxa-1-azaspiro[4.4]nonan-1-ylmethyl)phenoxy)azetidin-1-yl)(5-phenyl-1,3,4-oxadiazol-2-yl)methanone may be obtained by chiral chromatography.

Example 16

(3-(4-(2-oxa-5-azaspiro[3.4]octan-5-ylmethyl)-3-methoxyphenoxy)azetidin-1-yl)(5-phenyl-1,3,4-oxadiazol-2-yl)methanone

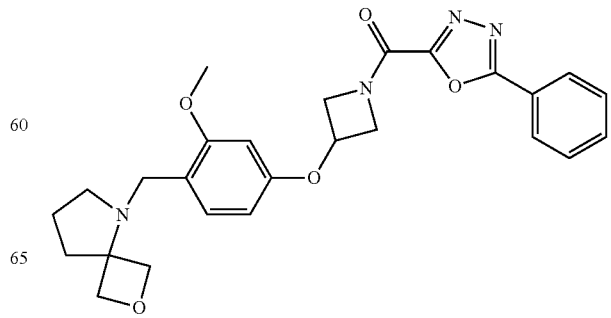

2-Oxa-5-azaspiro[3.4]octane TFA salt (0.111 g, ca. 70%, 0.34 mmol) and 2-methoxy-4-(1-(5-phenyl-1,3,4-oxadiazole-2-carbonyl)azetidin-3-yloxy)benzaldehyde (0.13 g, 0.34 mmol) were mixed in dichloromethane (2 ml). Triethylamine (0.1 ml, 0.72 mmol) was then added, followed by sodium triacetoxyhydroborate (0.145 g, 0.69 mmol). The mixture was stirred at ambient temperature overnight. LC-MS showed some remaining starting material. An additional amount of sodium triacetoxyhydroborate (0.11 g) was added and stirring was continued for 6 hours. The reaction mixture was then diluted with dichloromethane (10 ml) and shaken with NaHCO$_3$ (sat. 3 ml). The two phases were separated by the use of a phase separator. Evaporation of the organic phase afforded a colourless residue, which was was purified by preparative reverse-phase HPLC at pH 10 to give 0.113 g (69%) of the desired product as a solid. $^1$H NMR (600 MHz, DMSO) δ 1.58-1.66 (m, 2H), 2.07-2.12 (m, 2H), 2.55-2.58 (m, 2H), 3.81 (s, 3H), 3.88 (s, 2H), 4.08-4.12 (m, 1H), 4.44 (d, 2H), 4.54-4.58 (m, 1H), 4.64 (ddd, 1H), 4.79 (d, 2H), 5.10 (ddd, 1H), 5.19 (ddd, 1H), 6.42 (dd, 1H), 6.54 (d, 1H), 7.20 (d, 1H), 7.64-7.72 (m, 3H), 8.05-8.11 (m, 2H). MS (APCI+) m/z 477.2 [M+H]$^+$, LC purity: 93%

Example 17

(3-(4-(2-oxa-5-azaspiro[3.4]octan-5-ylmethyl)-2-methoxyphenoxy)azetidin-1-yl)(5-phenyl-1,3,4-oxadiazol-2-yl)methanone

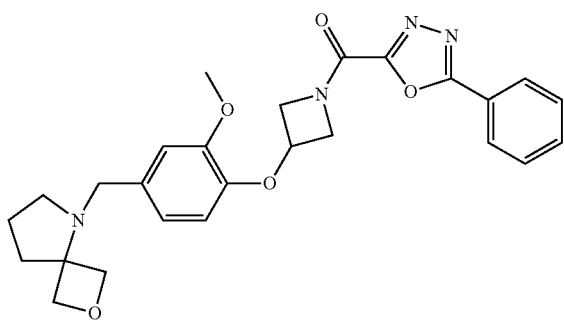 [SMILES: COc1cc(CN2CCCC23COC3)ccc1OC1CN(C(=O)c2nnc(-c3ccccc3)o2)C1]

Oxa-5-azaspiro[3.4]octane TFA salt (0.111 g, ca. 70%, 0.34 mmol) and 3-methoxy-4-(1-(5-phenyl-1,3,4-oxadiazole-2-carbonyl)azetidin-3-yloxy)benzaldehyde (0.13 g, 0.34 mmol) were mixed in dichloromethane (2 ml). Triethylamine (0.1 ml, 0.72 mol) was then added, followed by sodium triacetoxyhydroborate (0.145 g, 0.69 mmol). The mixture was stirred at ambient temperature overnight. LC-MS showed some remaining starting material. An additional amount of sodium triacetoxyhydroborate (0.1 g) was added and stirring was continued for 6 hours. The reaction mixture was then diluted with dichloromethane (10 ml) and shaken with NaHCO$_3$ (sat. 3 ml). The two phases were separated by the use of a phase separator. Evaporation of the organic phase afforded a residue, which was purified by preparative reverse-phase HPLC at pH 10 to give 0.107 g of the desired product as a solid. The obtained product was further purified by automated flash chromatography on a 10 g column. 3% of NH$_3$ (2M) in MeOH/EtOAc was used as the mobile phase. The product was detected by a UV detector at 274 nm. After evaporation of the solvent mixture was obtained 0.09 g (55%) of the desired product as a solid. $^1$H NMR (400 MHz, CDCl$_3$) δ 1.71 (dt, 2H), 2.18-2.24 (m, 2H), 2.60 (t, 2H), 3.89 (s, 3H), 3.97 (s, 2H), 4.39-4.47 (m, 1H), 4.57 (d, 2H), 4.63 (dd, 1H), 4.83 (t, 1H), 4.90 (d, 2H), 5.03-5.15 (m, 2H), 6.63 (d, 1H), 6.87 (d, 1H), 6.95 (s, 1H), 7.5-7.62 (m, 3H), 8.17 (d, 2H). MS (APCI+) m/z 477.3 [M+H]$^+$, LC purity: 97%.

Example 18

(3-(4-(2-oxa-5-azaspiro[3.4]octan-5-ylmethyl)-2-methoxyphenoxy)azetidin-1-yl)(5-(4-(difluoromethyl)phenyl)-1,3,4-oxadiazol-2-yl)methanone

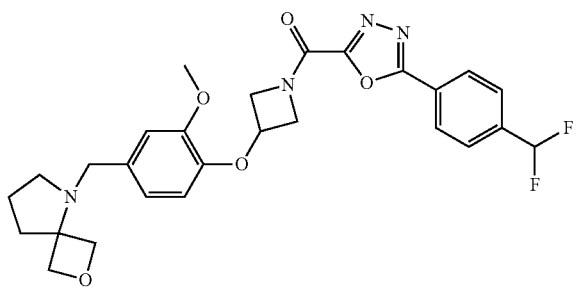 [SMILES: COc1cc(CN2CCCC23COC3)ccc1OC1CN(C(=O)c2nnc(-c3ccc(C(F)F)cc3)o2)C1]

2-Oxa-5-azaspiro[3.4]octane TFA salt (0.1.1 g, ca. 70%, 0.34 mmol) and 4-(1-(5-(4-(difluoromethyl)phenyl)-1,3,4-oxadiazole-2-carbonyl)azetidin-3-yloxy)-3-methoxybenzaldehyde (0.146 g, 0.34 mmol) were mixed in dichloromethane (2 ml). Triethylamine (0.1 ml, 0.72 mmol) was added, followed by sodium triacetoxyhydroborate (0.144 g, 0.68 mmol). The mixture was stirred at ambient temperature overnight (16 h). LC-MS showed some remaining starting material and an additional amount of sodium triacetoxyhydroborate (0.113 g) was added. Stirring continued for 6 h. The reaction mixture was then diluted with dichloromethane (10 ml) and shaken with NaHCO$_3$ (sat. 3 ml). The two phases were separated by the use of a phase separator. Evaporation of the organic phase afforded a residue, which was purified by preparative reverse-phase HPLC at pH 10 to give 0.112 g (62%) of the desired product as a solid.
$^1$H NMR (500 MHz, CDCl$_3$): δ $^1$H NMR (600 MHz, DMSO) δ 1.63 (dt, 2H), 2.13 (dd, 2H), 2.51-2.53 (m, 2H), 3.78 (d, 3H), 3.90 (d, 2H), 4.12 (dd, 1H), 4.43 (d, 2H), 4.60 (ddd, 2H), 4.80 (d, 2H), 5.04-5.12 (m, 2H), 6.78 (d, 1H), 6.87 (dd, 1H), 7.00 (d, 1H), 7.18 (t, 1H), 7.84 (d, 2H), 8.23 (d, 2H). MS (APCI+) nm/527.2 [M+H]$^+$, LC purity: 93%.

Example 19

(3-(4-(2-oxa-5-azaspiro[3.4]octan-5-ylmethyl)-3-methoxyphenoxy)azetidin-1-yl)(5-(4-(difluoromethyl)phenyl)-1,3,4-oxadiazol-2-yl)methanone

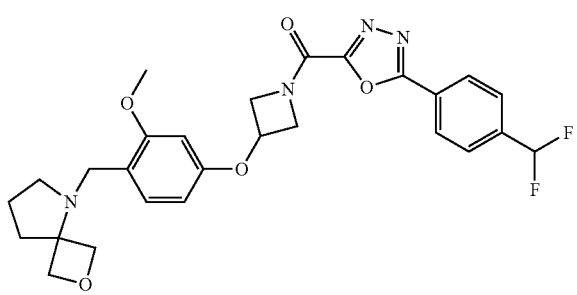 [SMILES: COc1cc(OC2CN(C(=O)c3nnc(-c4ccc(C(F)F)cc4)o3)C2)ccc1CN1CCCC12COC2]

2-Oxa-5-azaspiro[3.4]octane TFA salt (0.11 g, ca. 70%, 0.34 mmol) and 4-(1-(5-(4-(difluoromethyl)phenyl)-1,3,4-oxadiazole-2-carbonyl)azetidin-3-yloxy)-2-methoxybenzaldehyde (0.146 g, 0.34 mmol) were mixed in dichloromethane (2 ml). Triethylamine (0.1 ml, 0.72 mmol) was added, followed by sodium triacetoxyhydroborate (0.145 g, 0.68 mmol). The mixture was stirred at ambient temperature overnight. An LC-MS showed complete consumption of starting materials. The reaction mixture was then diluted with dichloromethane (10 ml) and shaken with NaHCO₃ (sat. 3 ml). The two phases were separated by the use of a phase separator. Evaporation of the organic phase afforded a residue, which was purified by preparative reverse-phase HPLC at pH 10 to give 0.119 g (67%) of the desired product as a solid. $^1$H NMR (500 MHz, CDCl₃): δ $^1$H NMR (600 MHz, DMSO) δ 1.56-1.68 (m, 2H), 2.06-2.14 (m, 2H), 2.55-2.58 (m, 2H), 3.81 (s, 3H), 3.88 (s, 2H), 4.11 (dd, 1H), 4.44 (d, 2H), 4.54-4.59 (m, 1H), 4.63-4.68 (m, 1H), 4.79 (d, 2H), 5.09-5.13 (m, 1H), 5.17-5.22 (m, 1H), 6.42 (dd, 1H), 6.54 (d, 1H), 7.18 (t, 1H), 7.21 (d, 1H), 7.85 (d, 2H), 8.23 (d, 2H). MS (APCI+) m/z 527.2 [M+H]⁺, LC purity: 97%.

Example 20

(3-(4-(6-Oxa-2-azaspiro[3.4]octan-2-ylmethyl)phenoxy)azetidin-1-yl)(5-(4-methoxyphenyl)-1,3,4-oxadiazol-2-yl)methanone

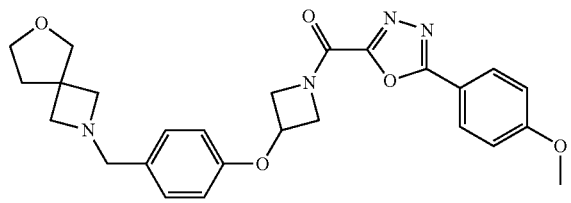 [SMILES: COc1ccc(-c2nnc(C(=O)N3CC(Oc4ccc(CN5CC6(CCOC6)C5)cc4)C3)o2)cc1]

Under an atmosphere of nitrogen and at room temperature, intermediate IIIE (16.1 g, 55.7 mmol) was dissolved in MeOH (150 mL). To the solution was added ethyl 5-(4-methoxyphenyl)-1,3,4-oxadiazole-2-carboxylate—for preparation, see e.g. *Journal für Praktische Chemie*, 327, 109-16 (1985)-(14.5 g, 58.5 mmol) in small portions within 5 minutes. The solution became turbid due to precipitation of product within 5 to 10 minutes of stirring. The suspension was stilled at RT for two days and the product was collected by filtration. The filter cake was washed with MeOH (5×50 ml) and the product was then dried in vacuum overnight at 40° C. There was obtained 25.7 g (97%) of the desired product as a solid. $^1$H NMR (400 MHz, DMSO-d₆): δ 1.88 (t, 2H), 2.99 (b, 4H), 3.37 (s, 2H), 3.54 (m, 4H), 3.76 (s, 3H), 3.92 (d, 1H), 4.44 (m, 2H), 4.99 (m, 2H), 6.72 (d, 2H), 7.09 (m, 4H), 7.90 (d, 2H). MS (APCI+) m/z 477.1 [M+H]⁺. LC purity: 99%.

This compound formed a crystalline hydrochloride salt and a crystalline mesylate salt using conventional methods.

Example 21

(3-(4-(1-Oxa-7-azaspiro[4.4]nonan-7-ylmethyl)phenoxy)azetidin-1-yl)(5-(4-methoxyphenyl)-1,3,4-oxadiazol-2-yl)methanone

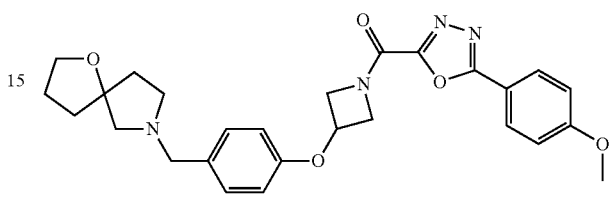

1-oxa-7-azaspiro[4.4]nonane hydrochloride (65 mg, 0.40 mmol) and TEA (0.082 mL, 0.59 mmol) were mixed with DCM (4 mL). To the mixture was added 4-(1-(5-(4-methoxyphenyl)-1,3,4-oxadiazole-2-carbonyl)azetidin-3-yloxy) benzaldehyde (0.150 g, 0.40 mmol) dissolved in DCM (1 mL). After stirring for 10 min, sodium triacetoxyhydroborate (0.168 g, 0.79 mmol) was added and the reaction mixture was stirred at RT overnight. An aqueous solution of NaHCO₃ (8%, 10 mL) was added and the mixture was extracted twice with DCM (15 mL). The organic layer was dried over a phase separator and concentrated under reduced pressure. The crude was purified by chromatography on silica gel (25 g) eluting with a mixture of EtOAc and ammonia in MeOH (2M) 20:1. The pooled fractions were concentrated under reduced pressure yielding the desired compound as a white solid (95 mg, 49%). $^1$H NMR (400 MHz, CDCl₃): δ 1.73 (m, 5H), 1.86 (m, 1H), 2.57 (m, 3H), 2.69 (m, 1H), 3.56 (m, 2H), 3.77 (m, 2H), 3.88 (s, 3H), 4.32 (dd, 1H), 4.63 (m, 1H), 4.73 (dd, 1H), 5.07 (m, 2H), 6.71 (d, 2H), 7.01 (d, 2H), 7.27 (d, 2H), 8.09 (d, 2H). MS (APCI+) m/z 491.5 [M+H]⁺. LC purity: 94%.

Example 22

(3-(4-(1-Oxa-7-azaspiro[4.4]nonan-7-ylmethyl)phenoxy)azetidin-1-yl)(5-phenyl-1,3,4-oxadiazol-2-yl)methanone

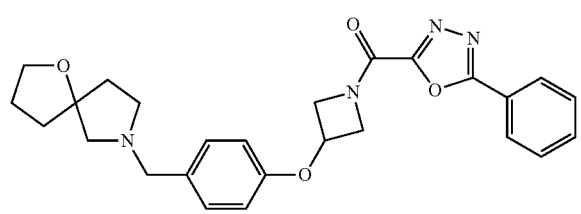 [SMILES: O=C(c1nnc(-c2ccccc2)o1)N1CC(Oc2ccc(CN3CCC4(CCCO4)C3)cc2)C1]

Using a similar protocol as described in Example 21 but employing 1-oxa-7-azaspiro[4.4]nonane hydrochloride (70 mg, 0.43 mmol) and 4-(1-(5-phenyl-1,3,4-oxadiazole-2-carbonyl)azetidin-3-yloxy)benzaldehyde (150 mg, 0.43 mmol) as starting materials afforded 103 mg (52%) of 22. $^1$H NMR (400 MHz, DMSO-d₆): δ 1.81 (m, 6H), 2.50 (m, 4H), 3.50 (m, 2H), 3.65 (m, 2H), 4.10 (dd, 1H), 4.56 (dd, 1H), 4.63 (dd, 1H), 5.10 (dd, 1H), 5.16 (m, 1H), 6.86 (d, 2H), 7.27 (d, 2H), 7.68 (m, 3H), 8.08 (d, 2H). LC purity: 95%.

Intermediate Aldehydes 4-(1-(5-(4-Methoxyphenyl)-1,3,4-oxadiazole-2-carbonyl) azetidin-3-yloxy)benzaldehyde was prepared as described in WO2010/125390.

Intermediate I 4-(1-(5-Phenyl-1,3,4-oxadiazole-2-carbonyl)azetidin-3-yloxy)benzaldehyde IA. (3-Hydroxyazetidin-1-yl)(5-phenyl-1,3,4-oxadiazol-2-yl)methanone

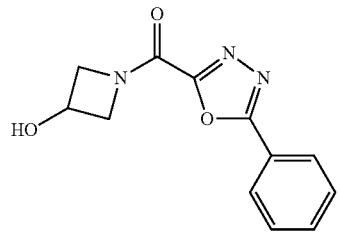 [SMILES: O=C(c1nnc(-c2ccccc2)o1)N1CC(O)C1]

To a clear solution of ethyl 5-phenyl-1,3,4-oxadiazole-2-carboxylate (0.40 g, 1.83 mmol) in dry methanol (5 mL) was added sodium cyanide (18 mg, 0.37 mmol). A solution of 3-hydroxyazetidine hydrochloride (0.45 g, 2.84 mmol) and triethylamine (0.40 mL, 2.84 mmol) in methanol (5 mL) was added at ambient temperature. After stirring for 20 min water (20 mL) and dichloromethane (30 mL) were added. The layers were separated and the aqueous phase was extracted twice with dichloromethane (30 mL). The combined organic layers were evaporated. The crude product was then treated with toluene (5 mL), filtered, washed with toluene (5 mL) and dried in vacuo. There was obtained 0.40 g (90%) of 53A as a solid. $^1$H NMR (400 MHz, DMSO-d$_6$): δ 3.84 (dd, 1H), 4.31 (m, 2H), 4.56 (m, 1H), 4.79 (dd, 1H), 5.87 (d, 1H), 7.64 (m, 3H), 8.05 (d, 2H), MS (APCI+) m/z 246 [M+H]$^+$.

IB. 1-(5-Phenyl-1,3,4-oxadiazole-2-carbonyl)azetidin-3-yl methanesulfonate

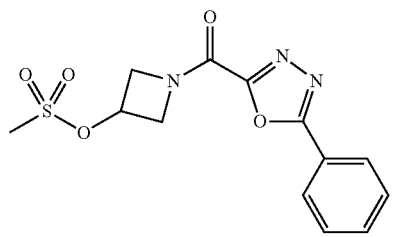 [SMILES: CS(=O)(=O)OC1CN(C(=O)c2nnc(-c3ccccc3)o2)C1]

A suspension of IA (2.00 g, 8.16 mmol) in dichloromethane (200 mL) was cooled in an ice-bath. Triethylamine (1.58 mL, 11.42 mmol) was added followed by methanesulfonyl chloride (0.85 mL, 11.01 mmol). After the addition, the cooling bath was removed. The mixture was stirred overnight and then transferred to a separatory funnel. The mixture was washed with water and then with aqueous NaHCO$_3$. The organic solution was dried (phase separator) and evaporated. There was obtained 2.58 g (98%) of 1-(5-phenyl-1,3,4-oxadiazole-2-carbonyl)azetidin-3-yl methanesulfonate as a solid. $^1$H NMR (500 MHz, CDCl$_3$): δ 3.13 (s, 3H), 4.43 (dd, 1H), 4.64 (dd, 1H), 4.87 (dd, 1H), 5.12 (dd, 1H), 5.40 (m, 1H), 7.54 (t, 2H), 7.59 (t, 1H), 8.15 (d, 2H), MS (APCI+) m/z 324 [M+H]$^+$.

IC. 4-(1-(5-Phenyl-1,3,4-oxadiazole-2-carbonyl) azetidin-3-yloxy)benzaldehyde

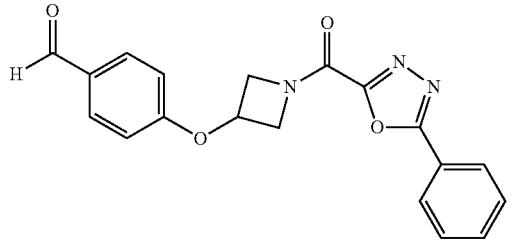 [SMILES: O=Cc1ccc(OC2CN(C(=O)c3nnc(-c4ccccc4)o3)C2)cc1]

4-Hydroxybenzaldehyde (1.10 g, 9.17 mmol), cesium carbonate (3.49 g, 10.70 mmol) and 1-(5-phenyl-1,3,4-oxadiazole-2-carbonyl)azetidin-3-yl methanesulfonate (IB) (2.70 g, 7.64 mmol) were mixed with DMF (80 mL). The mixture was stirred at 110° C. for 18 h and then cooled to RT. The solids were filtered off and the filtrate was evaporated. The residue was treated with methanol and the formed solid was collected by filtration. Drying under vacuum afforded 1.8 g (62%) of the title compound as a beige solid. $^1$H NMR (500 MHz, DMSO-d$_6$): δ 3.85 (s, 3H), 4.13 (dd, 1H), 4.57 (dd, 1H), 4.65 (dd, 1H), 5.12 (dd, 1H), 5.29 (m, 1H), 7.10 (d, 2H), 7.16 (d, 2H), 7.90 (d, 2H), 8.00 (d, 2H), 9.90 (s, 1H), MS (APCI+) m/z 380 [M+H]$^+$.

Intermediate II

2-Methyl-4-(1-(5-phenyl-1,3,4-oxadiazole-2-carbonyl)azetidin-3-yloxy)benzaldehyde

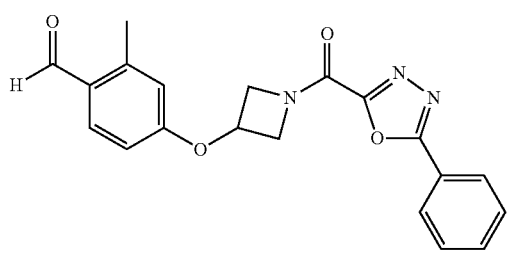 [SMILES: Cc1cc(OC2CN(C(=O)c3nnc(-c4ccccc4)o3)C2)ccc1C=O]

To a solution of 4-hydroxy-2-methylbenzaldehyde (0.11 g, 0.79 mmol) and 1-(5-phenyl-1,3,4-oxadiazole-2-carbonyl) azetidin-3-yl methanesulfonate (0.20 g, 0.62 mmol, Intermediate IB above) in DMF (10 mL) under nitrogen was added Cs$_2$CO$_3$ (0.24 g, 0.74 mmol). The mixture was stirred at 90° C. for 20 h, cooled to RT and then diluted with DCM. The solids were filtered off and the filtrate was evaporated. The product was purified on two occasions by preparative HPLC (Kromasil, C8) eluting with a gradient of acetonitrile and a mixture of acetic acid and water (0.2%). The pure fractions were combined and concentrated. The aqueous residues were extracted with DCM and the organic solutions were evaporated. There was obtained 162 mg (72%) of the title compound as a solid. $^1$H NMR (500 MHz, CDCl$_3$): δ 2.66 (s, 3H), 4.34 (d, 1H), 4.69 (dd, 1H), 4.76 (d, 1H), 5.17 (m, 2H), 6.64 (d, 1H), 6.72 (dd, 1H), 7.53 (t, 2H), 7.59 (t, 1H), 7.78 (d, 1H), 8.15 (d, 1H), 10.14 (s, 1H), MS (APCI+) m/z 364 [M+H]$^+$.

The following compounds were prepared by similar methods to those immediately above: 2-methoxy-4-(1-(5-phenyl-1,3,4-oxadiazole-2-carbonyl)azetidin-3-yloxy)benzaldehyde; 3-methoxy-4-(1-(5-phenyl-1,3,4-oxadiazole-2-carbonyl)azetidin-3-yloxy)benzaldehyde; and 4-(1-(5-(4-(difluoromethyl)phenyl)-1,3,4-oxadiazole-2-carbonyl)azetidin-3-yloxy)-3-methoxybenzaldehyde.

Intermediate III

IIIA. 2-Benzyl-6-oxa-2-azaspiro[3.4]octan-1-one

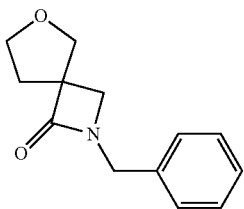 [SMILES: O=C1N(Cc2ccccc2)CC12CCOC2]

The reaction was performed in a 2-L round bottomed flask equipped with a thermometer and a scrubber containing an aqueous solution of NaOH (5 M, 500 mL). Under an atmosphere of nitrogen, DCM (1100 mL) and pyridine (2.27 mL, 26.7 mmol) were added to tetrahydrofuran-3-carboxylic acid (155 g, 1.34 mol). The mixture was heated to 25° C. using an external water-bath. Sulfurous dichloride (102 mL, 1.40 mol) was added during 15 min while stirring. The reaction temperature was maintained in the interval 25 to 27° C. during the addition. Gas evolution was observed when approximately one third of the sulfurous dichloride had been added. After the addition, the mixture was stirred at 25° C. for one hour and then at 30° C. for another hour whereupon more gas evolution was observed. The reaction mixture was then stirred at ambient temperature for 2 h and then cooled using a dry ice bath for approximately one hour until the temperature of the mixture became −72° C. Triethylamine (555 mL, 4.00 mol) was slowly added so that the temperature never exceeded −55° C. At the same time in a separate flask under nitrogen and at RT, 1,3,5-Tribenzyl-1,3,5-triazinane (162 g, 0.45 mol) was dissolved in DCM (250 mL) and to the resulting solution was slowly added (diethyloxonio)trifluoroborate (168 mL, 1.34 mol) during 5 min. After being stirred for 20 minutes at RT, the latter mixture was slowly added to the former mixture. The reaction temperature was never allowed to exceed −45° C. during the addition, which took about 20 min. The temperature was then slowly allowed to reach 0° C. using an external ice-bath. At the time when the temperature reached −10° C., there was a rapid increase in reaction temperature to about 12° C., which was compensated by further cooling the mixture. After the mixture had reached 0° C., the temperature was kept at 0° C. for 20 min. Water (500 ml) was added and the mixture was stirred overnight. The organic layer was washed with an aqueous solution of KHSO$_4$ (2 M, 500 ml) and then with water (500 ml). The solvent was removed by evaporation and the residual oil was then further concentrated using a rotavapor overnight. There was obtained 264 g (91%) of the desired intermediate IIIA with 95% assay as determined by NMR. $^1$H NMR (400 MHz, CDCl$_3$): δ 2.11 (m, 1H), 2.42 (m, 1H), 3.13 (d, 1H), 3.18 (d, 1H), 3.87 (m, 2H), 3.98 (m, 2H), 4.39 (m, 2H), 7.31 (m, 5H).

IIIB. 2-Benzyl-6-oxa-2-azaspiro[3.4]octane

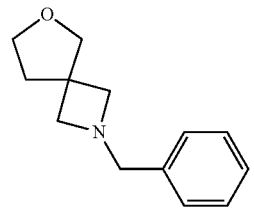 [SMILES: c1ccc(CN2CC3(CCOC3)C2)cc1]

A 3-L reactor, which had been dried at 50° C. overnight, was charged with anhydrous THF (900 mL). The solvent was cooled to −10° C. and aluminum trichloride (108 g, 0.813 mol) was added in small portions at such a rate that the temperature never exceeded 10° C. The addition took about 90 min, after which the temperature of the external oil-bath was adjusted to −5° C. After 30 min, a solution of lithium aluminum hydride (1.0 M in THF, 800 mL, 0.80 mol) was added during 40 min. The temperature never exceeded 10° C. during the addition. The resulting colourless solution was allowed to slowly warm-up to 19° C. during one hour. The mixture was kept at 19° C. for one additional hour and then it was cooled to 1° C. during a period of 25 min. Intermediate IIIA (149 g, 0.67 mol), dissolved in THF (200 mL), was added at such a rate that the temperature never exceeded 10° C. The addition was accomplished within 90 min and then the surfaces were rinsed with THF (50 mL). The external oil-bath was adjusted to 5° C. and after the reaction mixture had been stirred for one hour, EtOAc (80 mL, 0.82 mol) was added dropwise during 105 min. The reaction mixture was left overnight with external cooling, which had been adjusted to −10° C. After the mixture had been allowed to warm to 0° C., further EtOAc (15 mL, 0.15 mol) was added dropwise. The mixture was stirred at 5° C. for one hour and then cooled to 0° C. Ethanolamine (300 mL,) was added during one hour and then the temperature of the oil-bath gradually was adjusted to 20° C. The mixture was stirred for one day and then filtered. The filter cake was rinsed with TI-IF (2×1 L). The combined solutions were concentrated to dryness using a rotavapor. The residual oil was transferred to a separatory funnel with the aid of DCM (1500 mL) and water (500 mL). The phases were separated after one day. The organic solution was filtered through Celite® and then concentrated to an oil using a rotavapor. There was obtained 117 g (87%) of the desired intermediate IIIB with 90% assay as determined by NMR. $^1$H NMR (400 MHz, CDCl$_3$): δ 2.09 (t, 2H), 3.23 (m 4H), 3.61 (s, 2H), 3.76 (t, 2H), 3.83 (s, 2H), 7.27 (m, 5H), MS (APCI+) m/z 204.0 [M+H]$^+$.

IIIC. tert-Butyl 6-oxa-2-azaspiro[3.4]octane-2-carboxylate

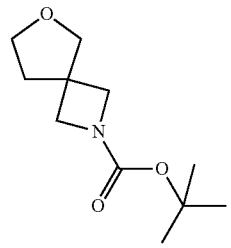

A 3-L reactor under nitrogen was charged with palladium on charcoal (52.4 g, 10%) together with a small amount of EtOH. Intermediate IIIB (50 g, 0.25 mol) was dissolved in EtOH (100 mL) and the resulting solution was added to the reactor, rinsing with EtOH (100 mL), and then adding further EtOH (1.8 L). Ammonium formiate (62 g, 0.98 mol), dissolved in water (100 mL), was added during 5 min, rinsing with additional water (400 mL). After the temperature had been adjusted to 50° C. during 30 nm, the mixture was stirred for 4 h. The temperature was adjusted to 20° C. during 40 min and then triethylamine was added during a couple of minutes. Di-tert-butyl dicarbonate (56.8 g, 0.26 mol) was added in six portions during 20 min. After stirring for 2 h, and after having added yet three additional portions of di-tert-butyl dicarbonate (totally, 11.5 g, 53 mmol), the mixture was filtered through Celite® (Seitz, K200). The solid material was rinsed with EtOH (2×500 mL) and the combined solutions were concentrated to dryness on a rotavapor. To the residue were added methyl tert-butyl ether (200 mL) and water (100 mL) and the resulting two-phase mixture was allowed to stand at ambient temperature overnight. The mixture was transferred to a separatory funnel with the aid of additional methyl tert-butyl ether (300 mL) and water (150 mL). The aqueous phase was neutralized to pH 7 by adding approximately 12 mL of an aqueous solution of NaOH (4 M). After the phases had been separated, the organic solution was filtered through Celite® (Seitz filter, K200) and then concentrated to dryness using a rotavapor. The residue was re-dissolved in methyl tert-butyl ether and the resulting solution was again concentrated to dryness. There was obtained 52.8 g (90%) of the desired intermediate IIIC as an oil with 82% assay as determined by NMR.

$^1$H NMR (400 MHz, CDCl$_3$): δ 1.43 (s, 9H), 2.10 (t, 2H), 3.81 (m, 4H), 3.87 (s, 4H).

IIID. tert-Butyl 3-(4-(6-oxa-2-azaspiro[3.4]octan-2-ylmethyl)phenoxy)azetidine-1-carboxylate

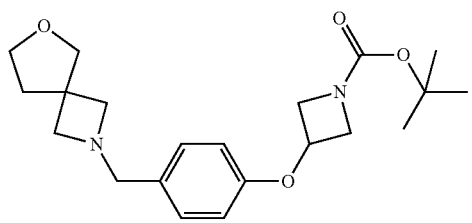 [SMILES: CC(C)(C)OC(=O)N1CC(Oc2ccc(CN3CC4(CCOC4)C3)cc2)C1]

Intermediate IIIC (260 g, 0.98 mol) was slowly added to TFA (500 ml) during 30 min. The temperature was kept between 18 and 20° C. during the addition with the aid of external cooling. The surfaces were rinsed with TFA (100 ml) and the temperature was then allowed to rise to 25° C. After stirring for 2 h, the mixture was transferred to a 20-L evaporation flask, rinsing with methanol. The mixture was concentrated and then co-evaporated with methanol (3×1 L) at 35° C. The residue was dissolved in EtOAc (2.5 L) and the resulting solution transferred to a 10-L reactor. DIPEA (455 g, 3.5 mol) was added followed by portion wise addition of tert-butyl 3-(4-formylphenoxy)azetidine-1-carboxylate (275 g, 0.99 mol). After the solution was cooled to 17° C., sodium triacetoxyhydroborate (255 g, 1.2 mol) was added and the mixture was then stirred at 27° C. for 20 h. Another portion of sodium triacetoxyhydroborate (54 g, 0.25 mol) was added. The mixture was stirred for another 24 h, diluted with water (1.35 L) and then evaporated at 35° C. After most of the organic solvent and some of the water had been evaporated, an aqueous solution of acetic acid (5%, 3.66 L) was added followed by a mixture of toluene (750 ml) and heptane (750 ml). After thorough mixing, the organic phase was removed and the aqueous solution was washed with a mixture of toluene (150 mL) and heptane (150 mL). MTBE (1000 ml) was added and the aqueous phase was pH adjusted to 9.5 by adding an aqueous solution of NaOH (50%, 403 g). The organic phase was isolated and to the aqueous phase was added another portion of NaOH (50%, 120 g) to give a pH of 9.74. The mixture was extracted with MTBE (1000 ml) and the combined organic solutions were dried over potassium carbonate, filtered through celite and then concentrated to 1.5 L. Heptane was added and the mixture was heated to 45° C., cooled to 35° C., then to 5° C. over 3 h and finally to 5° C. overnight. The mixture was filtered and the filter cake was washed with heptane (400 mL). After drying in vacuum overnight at 25° C., there was obtained 271 g (72%) of intermediate IIID as a solid. $^1$H NMR (400 MHz, methanol-d$_4$): δ 1.50 (s, 9H), 2.14 (t, 2H), 3.31 (m, 4H), 3.62 (s, 2H), 3.79 (t, 2H), 3.84 (s, 2H), 3.94 (m, 2H), 4.37 8 m, 2H), 5.00 (m, 1), 6.82 (d 2H), 7.28 (d, 2H), MS (APCI+) m/z 375.2 [M+H]$^+$.

IIIE. 2-(4-(Azetidin-3-yloxy)benzyl)-6-oxa-2-azaspiro[3.4]octane

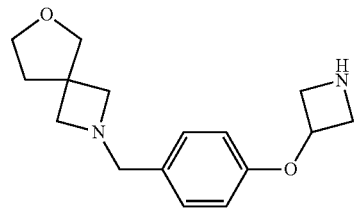 [SMILES: c1cc(OC2CNC2)ccc1CN1CC2(CCOC2)C1]

Intermediate IIID (23.2 g, 56 mmol)—which was prepared in a similar manner as above but contaminated with approximately 10% ethanol—was dissolved in DCM (70 mL). The solution was concentrated in order to remove most of the ethanol. To the residue was then added DCM (70 mL) at RT followed by a dropwise addition of TFA (12.6 mL, 169 mmol). The mixture was stirred for one hour and then a second portion of TFA (12.6 mL, 169 mmol) was added. After three additional hours of stirring—including the addition of yet two additional portions of TFA (2×12.6 mL, 169 mmol)—the mixture was cooled with an ice-bath and then an aqueous solution of sodium hydroxide (25%, 200 mL) was added slowly. The mixture was stirred vigorously for 10 min and then the two layers were separated. The aqueous layer was extracted three times with DCM (50 mL). The combined organic solutions were washed with water (50 ml) and then concentrated to an oil using a rotary evaporator. There was obtained 16 g (quantitative) of the desired intermediate IIIE with 95% assay as determined by NMR. $^1$H NMR (400 MHz, CDCl$_3$): δ 2.01 (t, 2H), 3.13 (m, 4H), 3.46 (s, 2H), 3.71 (m, 6H), 3.84 (m, 2H), 4.90 (m, 1H), 6.63 (m, 2H), 7.10 (m, 2H), MS (APCI+) m/z 275.1 [M+H]$^+$.

The invention claimed is:

1. A compound of formula I

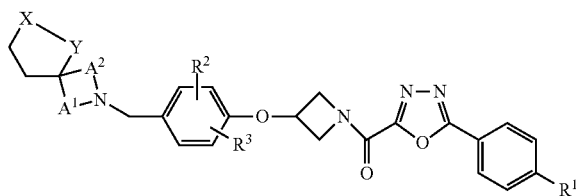

or a pharmaceutically acceptable salt thereof in which
- $R^1$ represents H, $C_{1-3}$alkoxy optionally substituted by one or more fluoro or a $C_{1-3}$alkyl group optionally substituted by one or more fluoro;
- $R^2$ and $R^3$ independently represent H, fluoro, chloro, bromo, a $C_{1-3}$alkyl group optionally substituted by one or more fluoro, or a $C_{1-3}$alkoxy group optionally substituted by one or more fluoro provided that $R^2$ and $R^3$ are not located meta to each other;
- $A^1$ represents a bond, $CH_2$ or $CH_2$—$CH_2$;
- $A^2$ represents a bond, $CH_2$, $CH_2$—$CH_2$ or $CH_2$—$CH_2$—$CH_2$; provided that the total number of carbons in $A^1$ and $A^2$ together is 2 or 3;
- X represents a bond, $CH_2$ or O; and
- Y represents a bond, $CH_2$ or O;
- with the provisos that 1) one and only one of X and Y is always O and 2) when $A^1$ and $A^2$ each represent $CH_2$ then one of X and Y is $CH_2$.

2. A compound of formula I according to claim 1 represented by formula IA

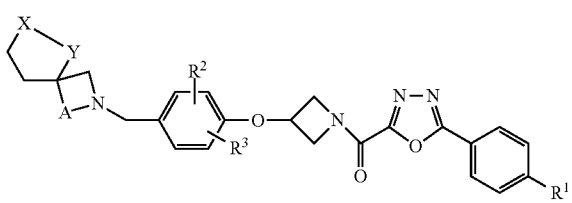

or a pharmaceutically acceptable salt thereof in which
- $R^1$ represents H, $C_{1-3}$alkoxy optionally substituted by one or more fluoro or a $C_{1-3}$alkyl group optionally substituted by one or more fluoro;
- $R^2$ and $R^3$ independently represent H, fluoro, chloro, bromo, a $C_{1-3}$alkyl group optionally substituted by one or more fluoro, or a $C_{1-3}$alkoxy group optionally substituted by one or more fluoro;
- A represents $CH_2$ or $CH_2$—$CH_2$;
- X represents a bond, $CH_2$ or O; and
- Y represents a bond, $CH_2$ or O;
- with the provisos that 1) one and only one of X and Y is always O and 2) when A is $CH_2$ and one of X and Y is O then the other one of X and Y is $CH_2$.

3. A compound of formula I according to claim 1 represented by formula II

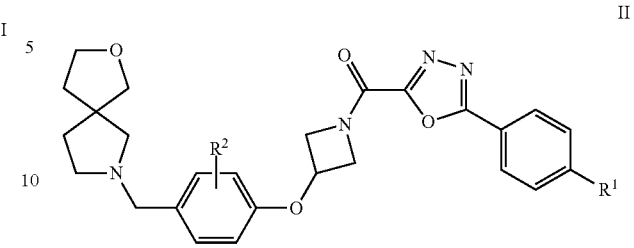

or a pharmaceutically acceptable salt thereof in which
- $R^1$ represents H, methoxy or difluoromethyl; and
- $R^2$ represents H, methyl or methoxy.

4. A compound of formula I according to claim 1 represented by formula IIA

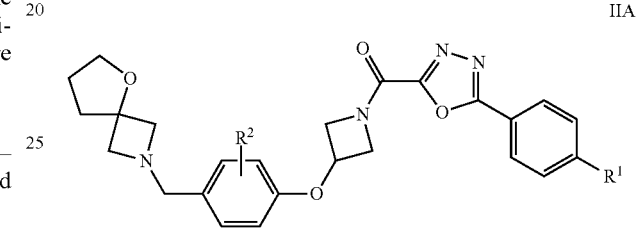

or a pharmaceutically acceptable salt thereof in which
- $R^1$ represents H, methoxy or difluoromethyl; and
- $R^2$ represents H, methyl or methoxy.

5. A compound of formula I according to claim 1 represented by formula IIB

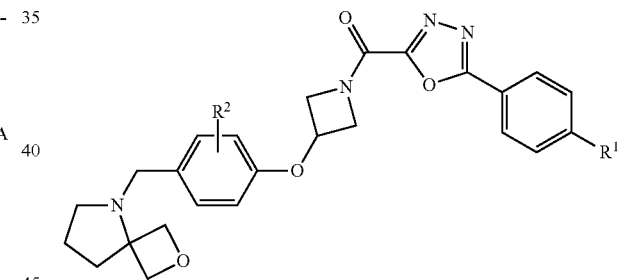

or a pharmaceutically acceptable salt thereof in which
- $R^1$ represents H, methoxy or difluoromethyl; and
- $R^2$ represents H, methyl or methoxy.

6. A compound of formula I according to claim 1 represented by formula IIC

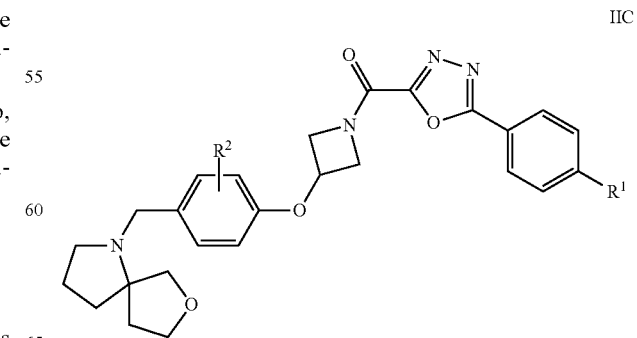

or a pharmaceutically acceptable salt thereof in which

R¹ represents H, methoxy or difluoromethyl; and
R² represents H, methyl or methoxy.

7. A compound of formula I according to claim 1 represented by formula IID

IID or a pharmaceutically acceptable salt thereof in which
R¹ represents H, methoxy or difluoromethyl; and
R² represents H, methyl or methoxy.

8. A compound of formula I according to claim 1 represented by formula IIE

IIE or a pharmaceutically acceptable salt thereof in which
R¹ represents H, methoxy or difluoromethyl; and
R² represents H, methyl or methoxy.

9. A compound according to claim 1 selected from one or more of the following compounds:
  (3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone;
  (+)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone;
  (−)-(3-(4-(2-oxa-7-azaspiro[4.4]nonan-7-ylmethyl)phenoxy)azetidin-1-yl)(5-(4-methoxyphenyl)-1,3,4-oxadiazol-2-yl)methanone;
  (3-(4-(5-oxa-2-azaspiro[3.4]octan-2-ylmethyl)phenoxy)azetidin-1-yl)(5-(4-methoxyphenyl)-1,3,4-oxadiazol-2-yl)methanone;
  (3-(4-(6-oxa-2-azaspiro[3.4]octan-2-ylmethyl)phenoxy)azetidin-1-yl)(5-(4-methoxyphenyl)-1,3,4-oxadiazol-2-yl)methanone;
  (3-(4-(2-oxa-7-azaspiro[4.4]nonan-7-ylmethyl)phenoxy)azetidin-1-yl)(5-phenyl-1,3,4-oxadiazol-2-yl)methanone;
  (+)-(3-(4-(2-oxa-7-azaspiro[4.4]nonan-7-ylmethyl)phenoxy)azetidin-1-yl)(5-phenyl-1,3,4-oxadiazol-2-yl)methanone;
  (−)- (3-(4-(2-oxa-7-azaspiro[4.4]nonan-7-ylmethyl)phenoxy)azetidin-1-yl)(5-phenyl-1,3,4-oxadiazol-2-yl)methanone;
  (3-(4-(6-oxa-2-azaspiro[3.4]octan-2-ylmethyl)phenoxy)azetidin-1-0(5-phenyl-1,3,4-oxadiazol-2-yl)methanone;
  (3-(4-(5-oxa-2-azaspiro[3.4]octan-2-ylmethyl)phenoxy)azetidin-1-0(5-phenyl-1,3,4-oxadiazol-2-yl)methanone;
  (3-(4-(6-oxa-2-azaspiro[3.4]octan-2-ylmethyl)-3-methylphenoxy)azetidin-1-0(5-phenyl-1,3,4-oxadiazol-2-yl)methanone;
  (3-(4-(2-oxa-7-azaspiro[4.4]nonan-7-ylmethyl)-3-methylphenoxy)azetidin-1-0(5-phenyl-1,3,4-oxadiazol-2-yl)methanone;
  (+)-(3-(4-(2-oxa-7-azaspiro[4.4]nonan-7-ylmethyl)-3-methylphenoxy)azetidin-1-0(5-phenyl-1,3,4-oxadiazol-2-yl)methanone;
  (−)-(3-(4-(2-oxa-7-azaspiro[4.4]nonan-7-ylmethyl)-3-methylphenoxy)azetidin-1-0(5-phenyl-1,3,4-oxadiazol-2-yl)methanone;
  (3-(4-(5-oxa-2-azaspiro[3.4]octan-2-ylmethyl)-3-methylphenoxy)azetidin-1-0(5-phenyl-1,3,4-oxadiazol-2-yl)methanone;
  (3-(4-(2-oxa-5-azaspiro[3.4]octan-5-ylmethyl)phenoxy)azetidin-1-0(5-(4-methoxyphenyl)-1,3,4-oxadiazol-2-yl)methanone;
  (3-(4-(2-oxa-5-azaspiro[3.4]octan-5-ylmethyl)phenoxy)azetidin-1-0(5-phenyl-1,3,4-oxadiazol-2-yl)methanone;
  (3-(4-(7-oxa-1-azaspiro[4.4]nonan-1-ylmethyl)phenoxy)azetidin-1-0(5-(4-methoxyphenyl)-1,3,4-oxadiazol-2-yl)methanone;
  (+)-(3-(4-(7-oxa-1-azaspiro[4.4]nonan-1-ylmethyl)phenoxy)azetidin-1-0(5-(4-methoxyphenyl)-1,3,4-oxadiazol-2-yl)methanone;
  (−)-(3-(4-(7-oxa-1-azaspiro[4.4]nonan-1-ylmethyl)phenoxy)azetidin-1-0(5-(4-methoxyphenyl)-1,3,4-oxadiazol-2-yl)methanone;
  (3-(4-(7-oxa-1-azaspiro[4.4]nonan-1-ylmethyl)phenoxy)azetidin-1-0(5-phenyl-1,3,4-oxadiazol-2-yl)methanone;
  (+)-(3-(4-(7-oxa-1-azaspiro[4.4]nonan-1-ylmethyl)phenoxy)azetidin-1-0(5-phenyl-1,3,4-oxadiazol-2-yl)methanone;
  (−)-(3-(4-(7-oxa-1-azaspiro[4.4]nonan-1-ylmethyl)phenoxy)azetidin-1-yl)(5-phenyl-1,3,4-oxadiazol-2-yl)methanone;
  (3-(4-(2-oxa-5-azaspiro[3.4]octan-5-ylmethyl)-3-methoxyphenoxy)azetidin-1-yl)(5-phenyl-1,3,4-oxadiazol-2-yl)methanone;
  (3-(4-(2-oxa-5-azaspiro[3.4]octan-5-ylmethyl)-2-methoxyphenoxy)azetidin-1-yl)(5-phenyl-1,3,4-oxadiazol-2-yl)methanone;
  (3-(4-(2-oxa-5-azaspiro[3.4]octan-5-ylmethyl)-2-methoxyphenoxy)azetidin-1-yl)(5-(4-(difluoromethyl)phenyl)-1,3,4-oxadiazol-2-yl)methanone;
  (3-(4-(2-oxa-5-azaspiro[3.4]octan-5-ylmethyl)-3-methoxyphenoxy)azetidin-1-yl)(5-(4-(difluoromethyl)phenyl)-1,3,4-oxadiazol-2-yl)methanone;
  (3-(4-(1-oxa-7-azaspiro[4.4]nonan-7-ylmethyl)phenoxy)azetidin-1-yl)(5-(4-methoxyphenyl)-1,3,4-oxadiazol-2-yl)methanone; and
  (3-(4-(1-oxa-7-azaspiro[4.4]nonan-7-ylmethyl)phenoxy)azetidin-1-yl)(5-phenyl-1,3,4-oxadiazol-2-yl)methanone;
or a pharmaceutically acceptable salt thereof.

10. A pharmaceutical composition comprising at least one compound according to claim 1 and a pharmaceutically acceptable carrier and/or diluent.

11. A method for treating obesity comprising administering to a warm-blooded animal in need of such treatment a therapeutically-effective amount of a compound according to claim 1.

12. A process for the preparation of a compound of formula I as described in claim 1 comprising a) reacting a compound of formula III

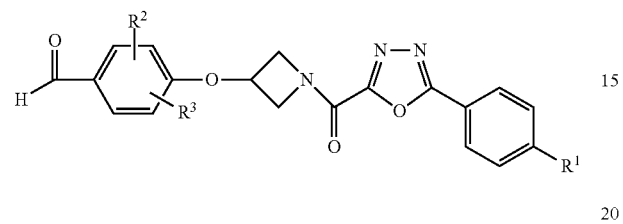

III in which $R^1$, $R^2$ and $R^3$ are as previously defined with a compound of formula IV

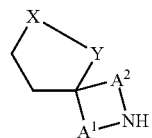

IV or a salt thereof in which $A^1$, $A^2$, X and Y are as previously defined in the presence of a reducing agent, in an appropriate solvent, and optionally, in the presence of a base if a salt of IV is used, at a temperature in the range of 0 to 150° C.; or b) reacting a compound of formula V

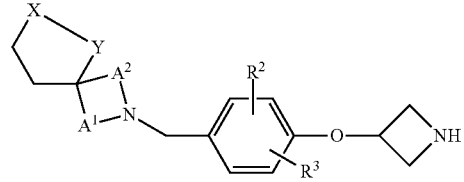

V in which $R^2$, $R^3$, $A^1$, $A^2$, X and Y are as previously defined with a compound of formula VI

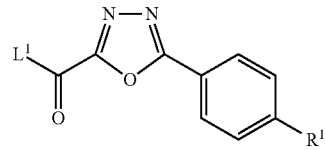

VI in which $R^1$ is as previously defined and $L^1$ represents a leaving group, in an appropriate solvent at a temperature in the range of 0 to 150° C.

13. An intermediate compound of formula V

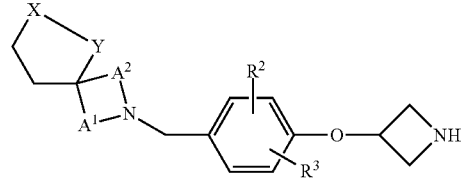

V in which $R^2$, $R^3$, $A^1$, $A^2$, X and Y are as defined in claim 1.

* * * * *